(12) United States Patent  
Tani et al.

(10) Patent No.: US 10,842,564 B2  
(45) Date of Patent: Nov. 24, 2020

(54) MICROWAVE SURGICAL INSTRUMENT

(75) Inventors: Tohru Tani, Otsu (JP); Shigeyuki Naka, Otsu (JP); Hisanori Shiomi, Otsu (JP)

(73) Assignee: National University Corporation Shiga University of Medical Science, Otsu (JP)

(*) Notice: Subject to any disclaimer, the term of this patent is extended or adjusted under 35 U.S.C. 154(b) by 311 days.

(21) Appl. No.: 14/238,167

(22) PCT Filed: Aug. 9, 2012

(86) PCT No.: PCT/JP2012/070404  
§ 371 (c)(1),  
(2), (4) Date: Feb. 10, 2014

(87) PCT Pub. No.: WO2013/022077  
PCT Pub. Date: Feb. 14, 2013

(65) Prior Publication Data  
US 2014/0194865 A1    Jul. 10, 2014

(30) Foreign Application Priority Data

Aug. 10, 2011 (JP) ................. 2011-174602  
Aug. 22, 2011 (JP) ................. 2011-180042

(51) Int. Cl.  
*A61B 18/18* (2006.01)  
*A61B 18/00* (2006.01)

(52) U.S. Cl.  
CPC .. *A61B 18/1815* (2013.01); *A61B 2018/0063* (2013.01); *A61B 2018/00446* (2013.01);  
(Continued)

(58) Field of Classification Search  
CPC .......... A61B 18/085; A61B 2018/1442; A61B 2018/1861; A61F 7/007; A61F 7/0088  
See application file for complete search history.

(56) References Cited

U.S. PATENT DOCUMENTS 5,369,367 A * 11/1994 Eisenhart ............... H01P 5/103  
                                                    324/632  
5,507,743 A    4/1996 Edwards et al.  
(Continued)

FOREIGN PATENT DOCUMENTS

JP       60-24835 A      2/1985  
JP       58-146177       4/1985  
(Continued)

OTHER PUBLICATIONS

A machine translation of the Office Action of the corresponding Japanese Patent Application dated Nov. 29, 2016.

*Primary Examiner* — Michael F Peffley  
*Assistant Examiner* — Bo Ouyang  
(74) *Attorney, Agent, or Firm* — Don D. Cha; HDC IP Law, LLP

(57) ABSTRACT

It is an object to provide a surgical instrument capable of locally applying microwaves to a minute biological tissue. It has been found that microwaves can be transmitted to a tip of a tapered coaxial body (9) and that microwaves are radiated from the entire central conductor exposed in a major axis direction by decreasing a sectional area (preferably diameter) of a central conductor (1) and a sectional area (preferably inner diameter) of an external conductor gradually or in a step-by-step manner with a ratio between the sectional area (diameter) of the central conductor (1) and the sectional area (inner diameter) of the external conductor being set to be constant, thereby achieving the present invention.

20 Claims, 16 Drawing Sheets

(52) U.S. Cl.
CPC ............... *A61B 2018/00589* (2013.01); *A61B 2018/1838* (2013.01)

(56) References Cited

U.S. PATENT DOCUMENTS

| | | | |
|---|---|---|---|
| 6,267,761 B1 | 7/2001 | Ryan | |
| 6,878,147 B2* | 4/2005 | Prakash | A61B 18/18 606/33 |
| 2002/0156470 A1* | 10/2002 | Shadduck | A61B 18/1485 606/41 |
| 2003/0038688 A1* | 2/2003 | Mitrovic | H01J 37/32211 333/34 |
| 2005/0027335 A1* | 2/2005 | Wakino | A61B 18/1815 607/96 |
| 2006/0158122 A1* | 7/2006 | Staines | H03B 1/02 315/39 |
| 2006/0271038 A1* | 11/2006 | Johnson | A61B 17/07207 606/45 |
| 2007/0054539 A1 | 3/2007 | Wakikaido | |
| 2009/0204112 A1* | 8/2009 | Kleyman | A61B 18/1815 606/33 |
| 2010/0249769 A1* | 9/2010 | Nau, Jr. | A61B 18/18 606/33 |
| 2011/0071428 A1* | 3/2011 | Frecker | A61B 10/0266 600/566 |
| 2011/0238055 A1* | 9/2011 | Kim | A61B 18/1815 606/33 |
| 2013/0041361 A1* | 2/2013 | Keller | A61B 5/0507 606/33 |

FOREIGN PATENT DOCUMENTS

| | | | |
|---|---|---|---|
| JP | 5-84255 A | 4/1993 | |
| JP | 2005-21658 A | 1/2005 | |
| JP | 2008-142467 A | 12/2006 | |
| JP | 2008-54925 A | 3/2008 | |
| JP | 2008-054926 A | 3/2008 | |
| JP | 2008-508964 A | 3/2008 | |
| JP | 2008054926 | * 3/2008 | ............ A61B 18/18 |
| JP | 2008-54926 A | 10/2008 | |
| JP | 2010-527704 A | 8/2010 | |
| WO | 2008-147773 A1 | 12/2008 | |

* cited by examiner

[Fig.1]
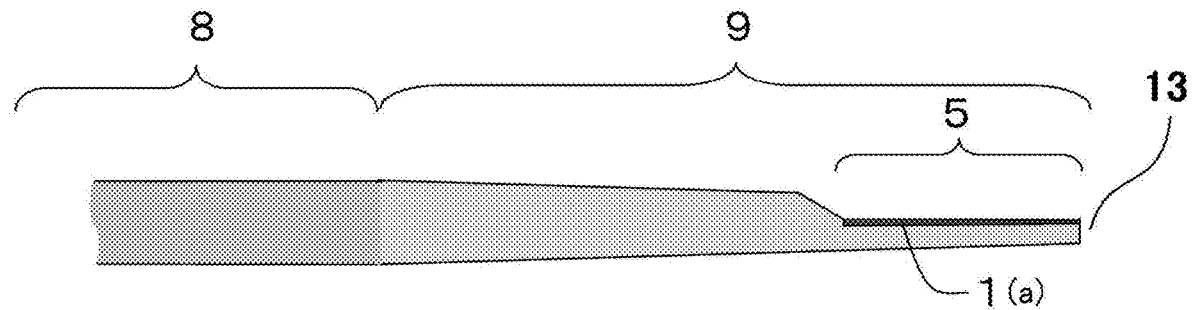
[Fig.2]
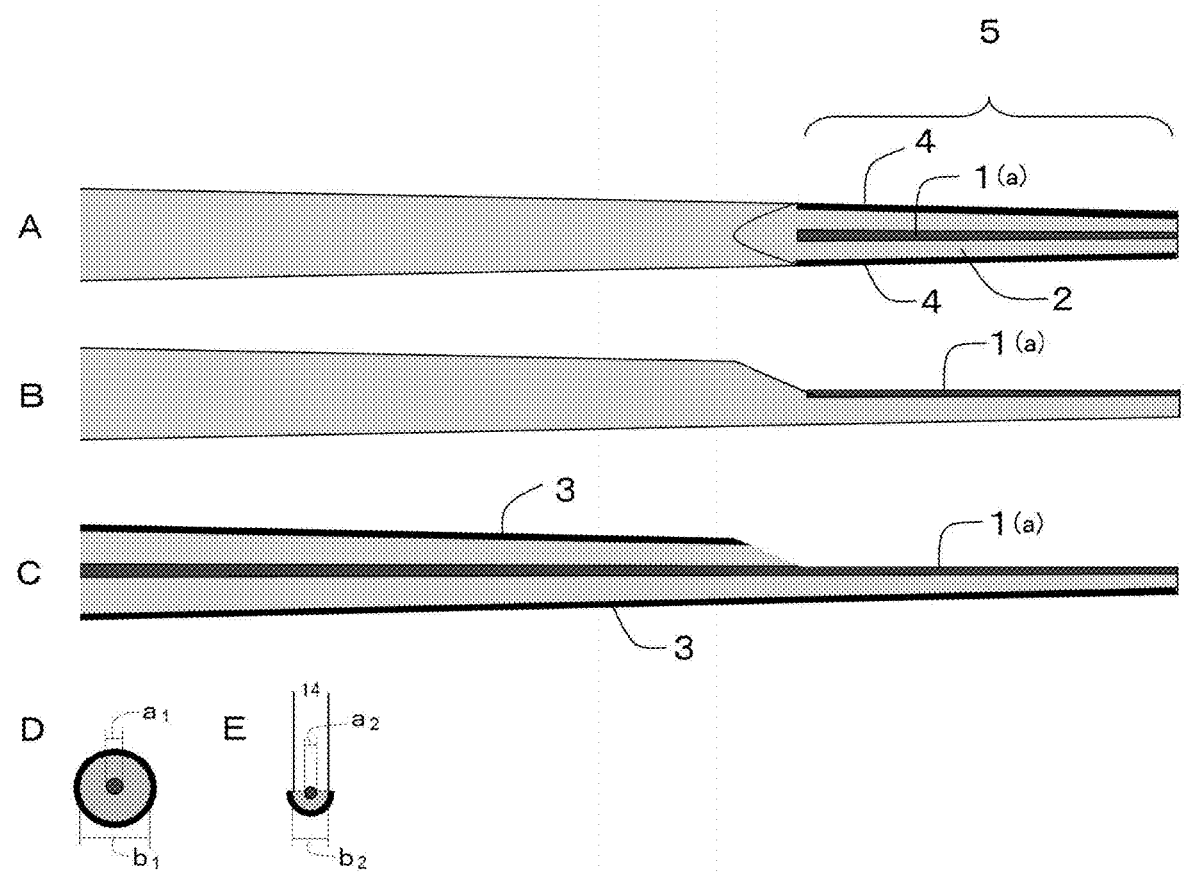

[Fig.3]
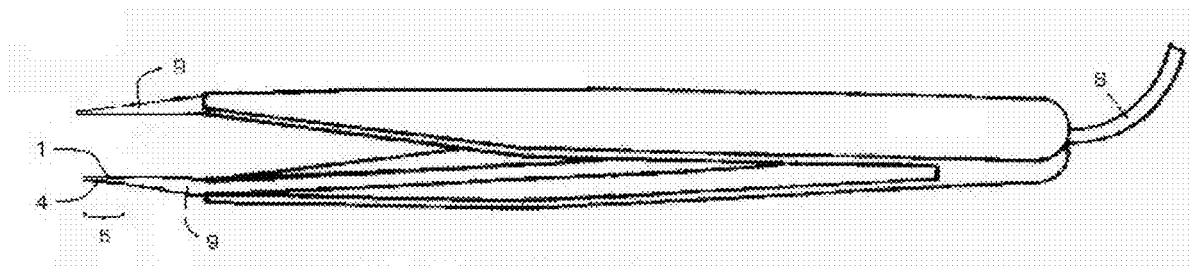
[Fig.4]
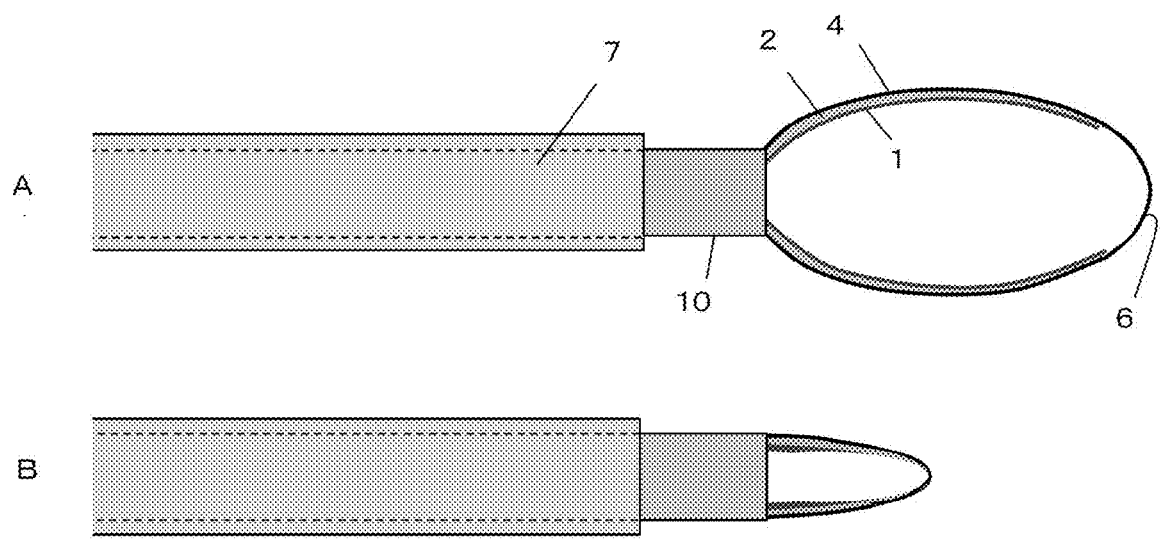
[Fig.5]
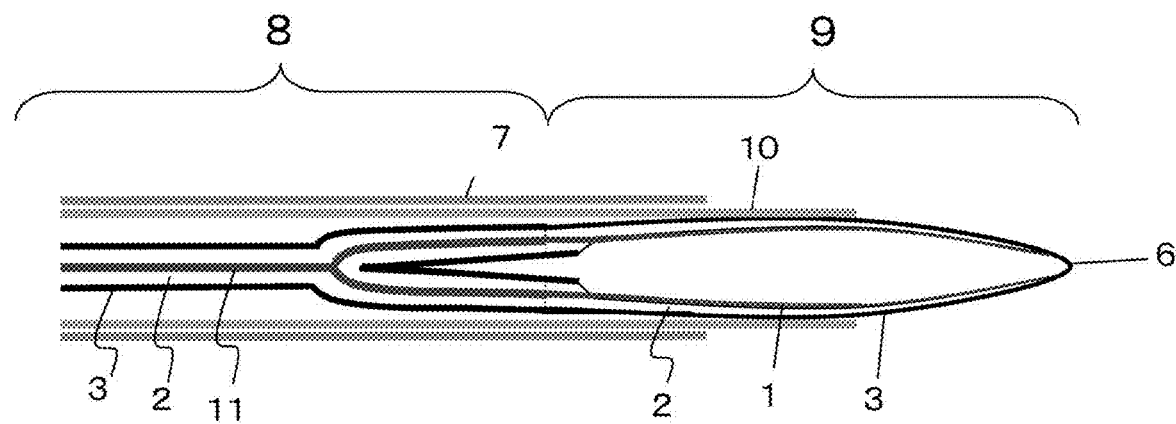

[Fig.6]
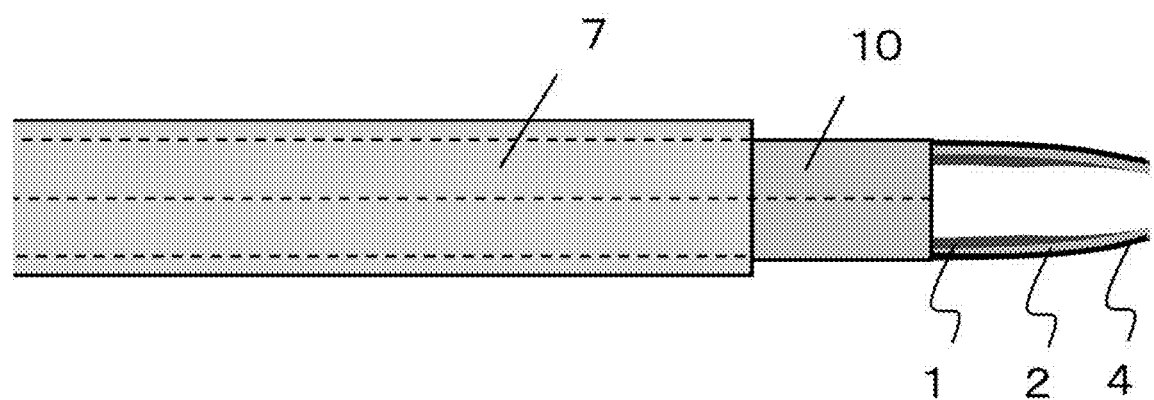
[Fig.7]
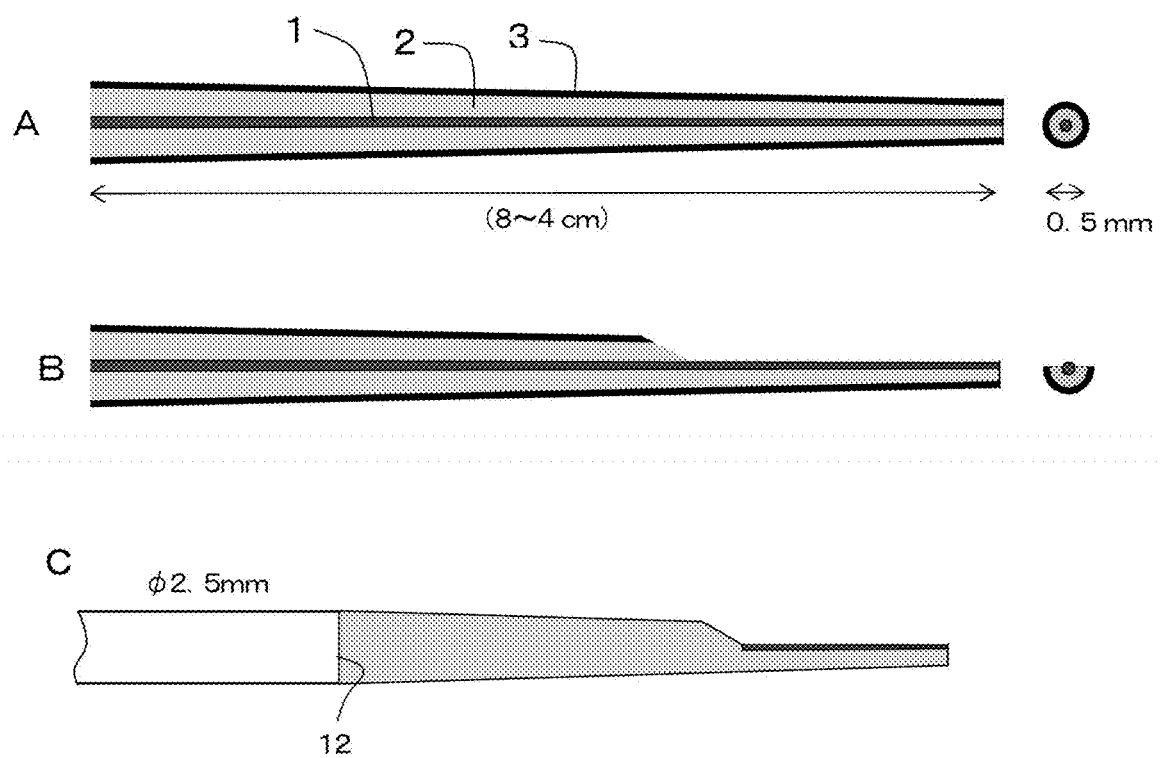

[Fig.8]
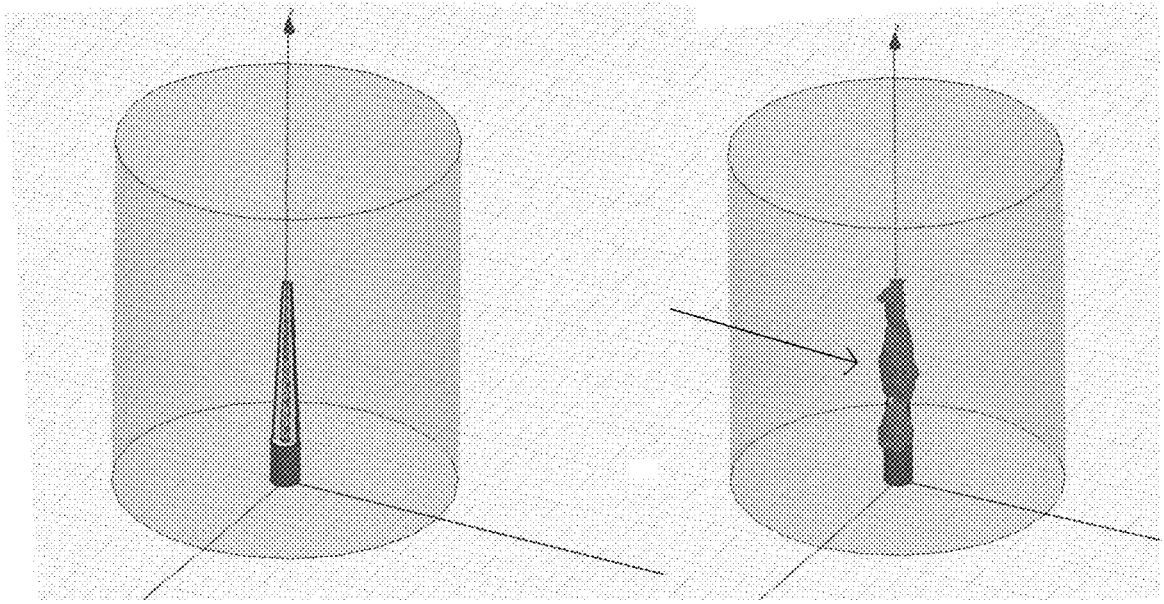
[Fig.9]
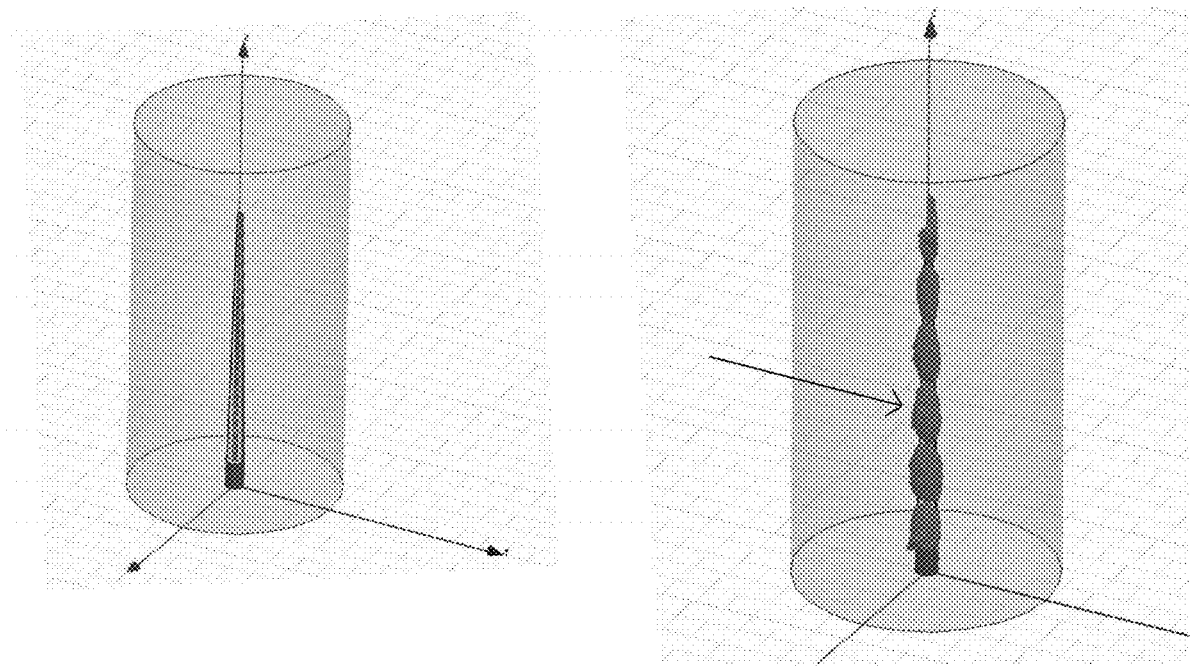

[Fig.10]
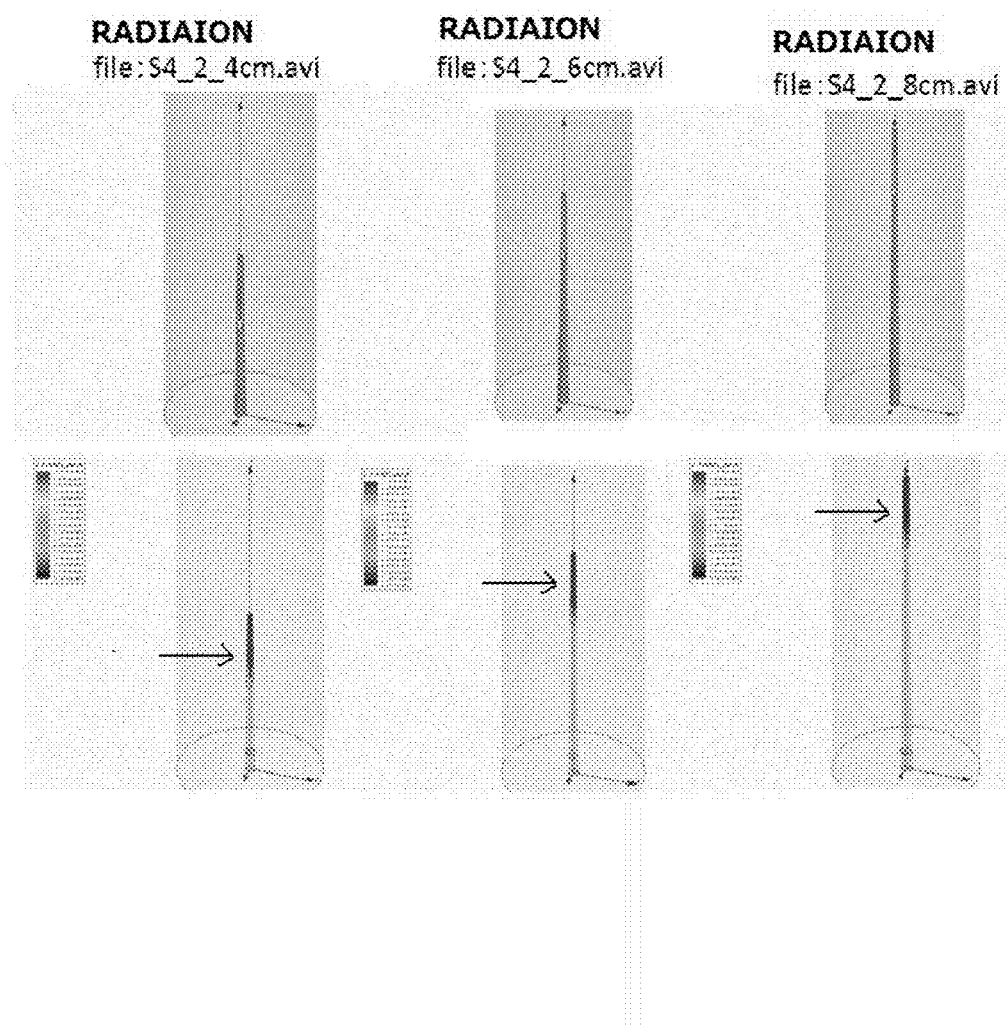

[Fig.11]
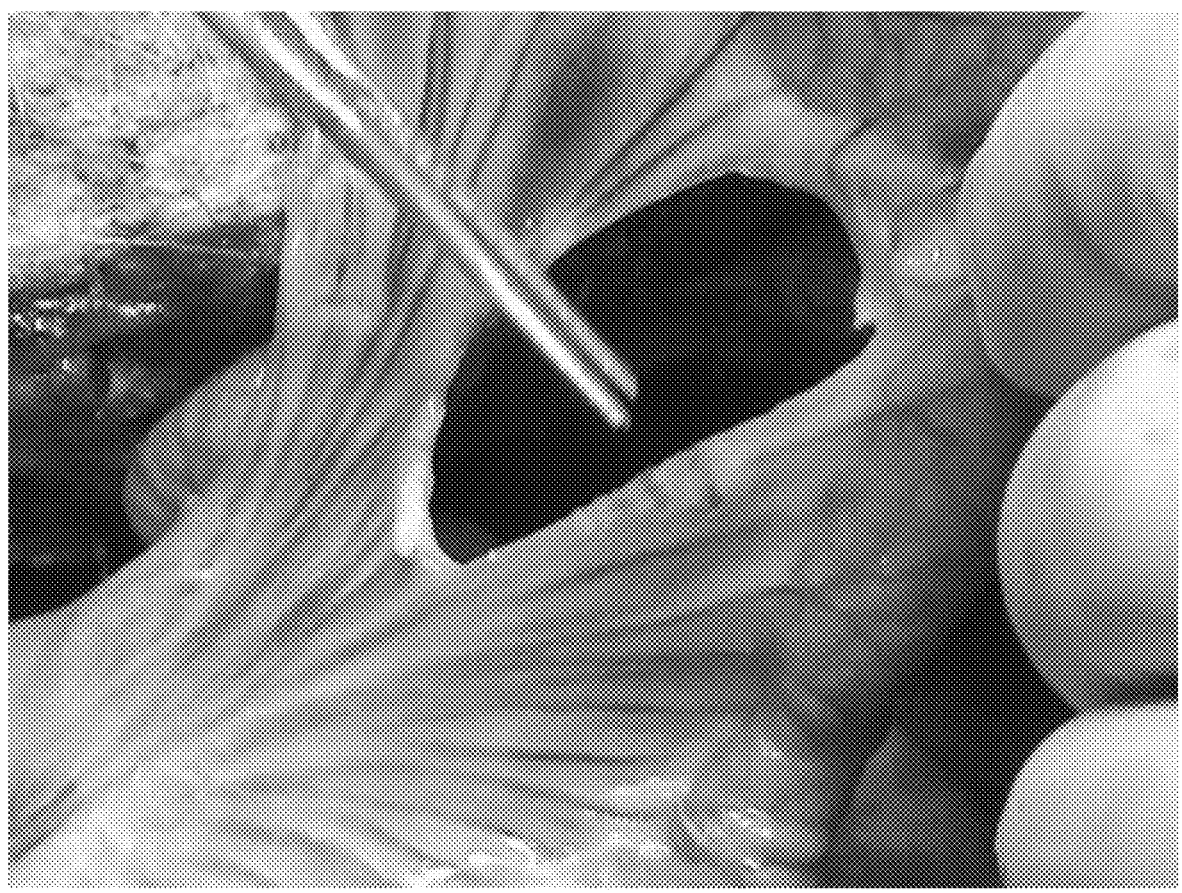

[Fig.12]
A
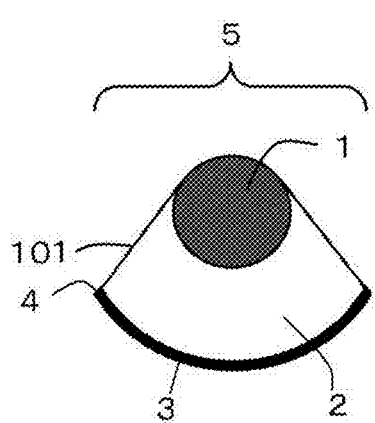
B
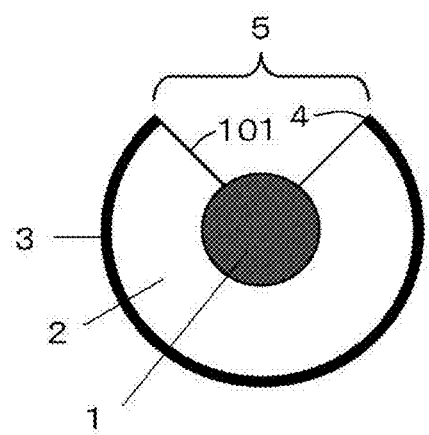
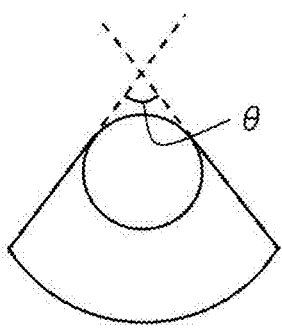
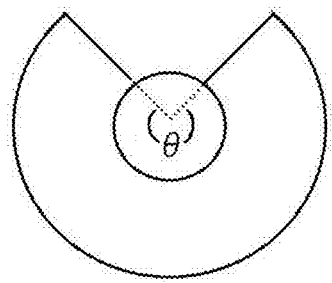

[Fig.13]
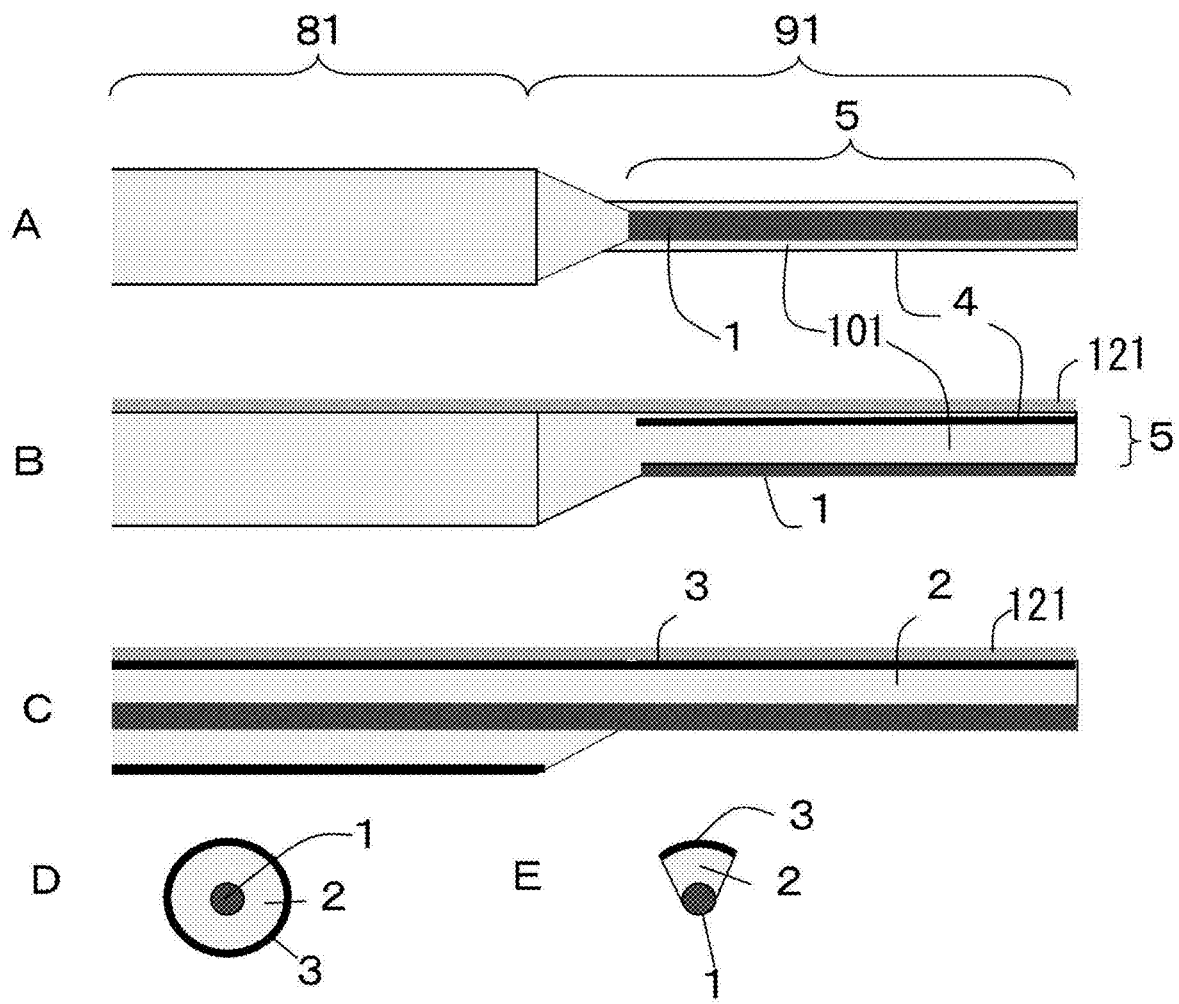

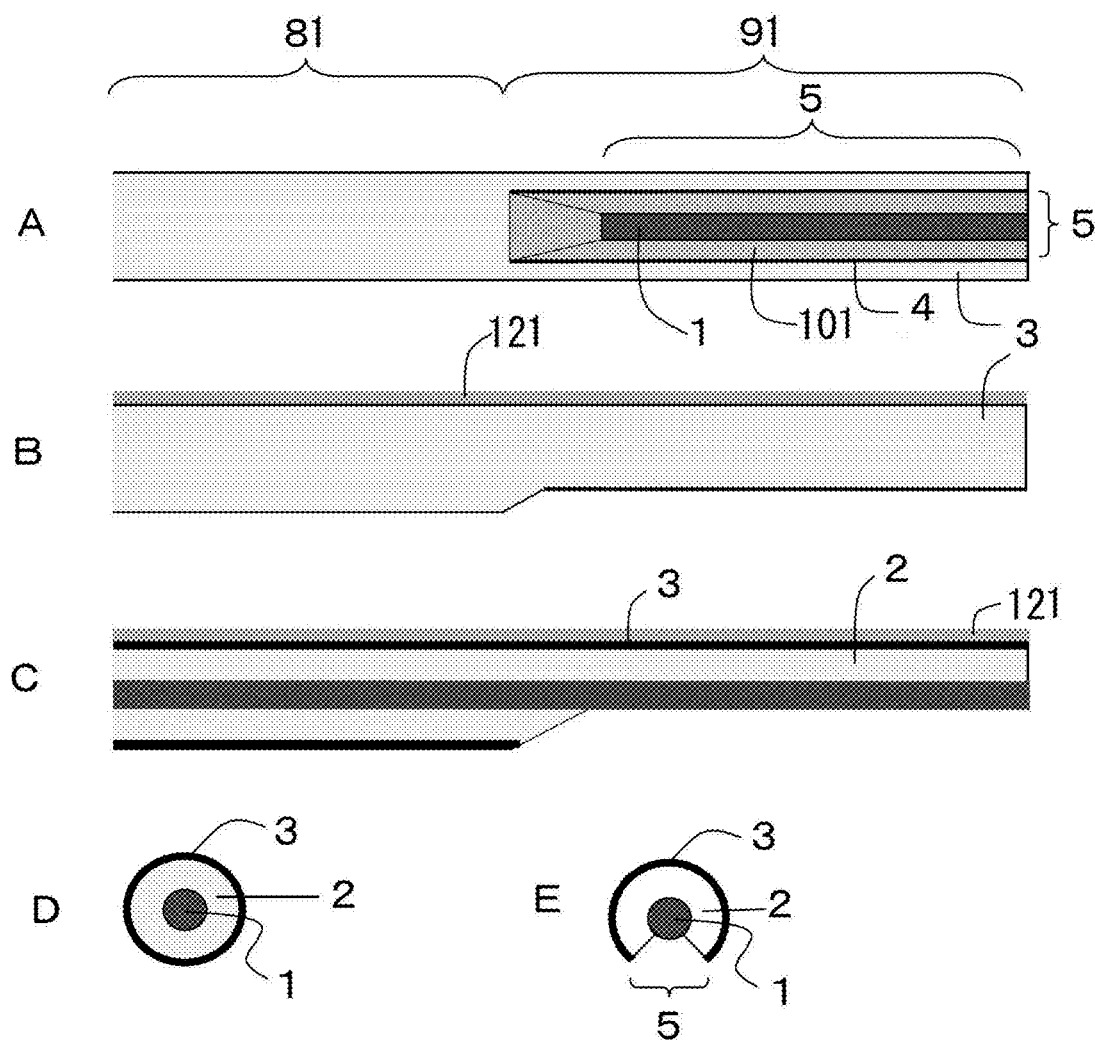
[Fig.14]

[Fig.15]
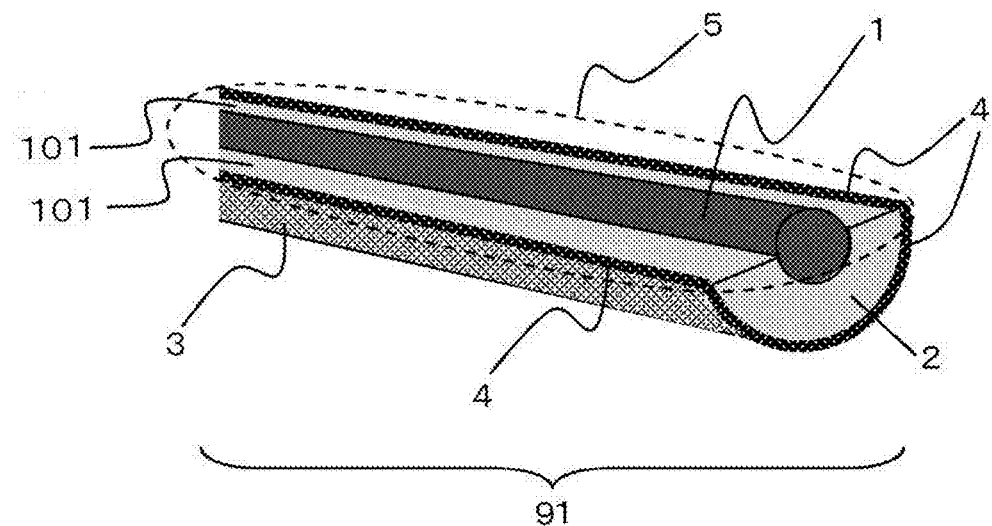
[Fig.16]
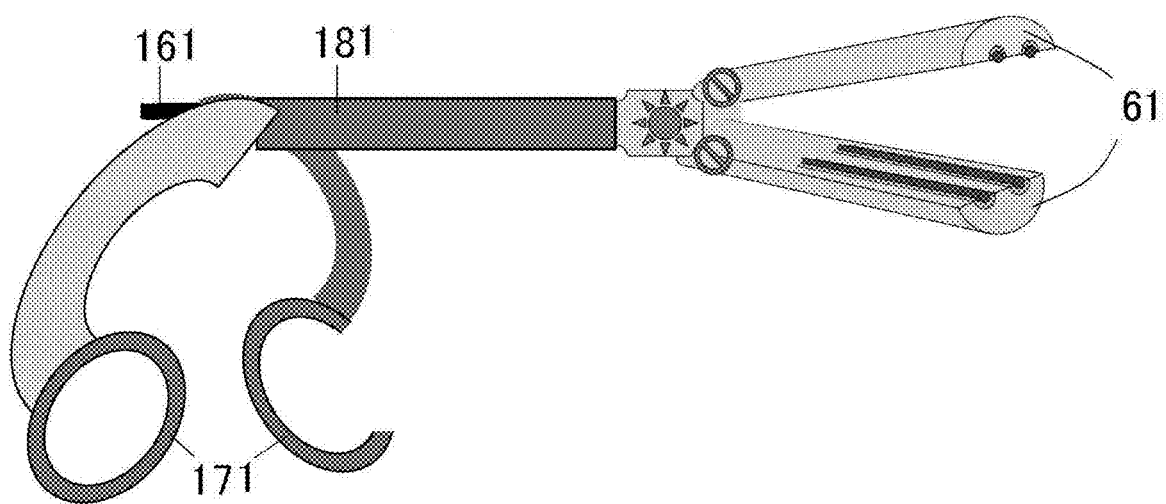

[Fig.17]
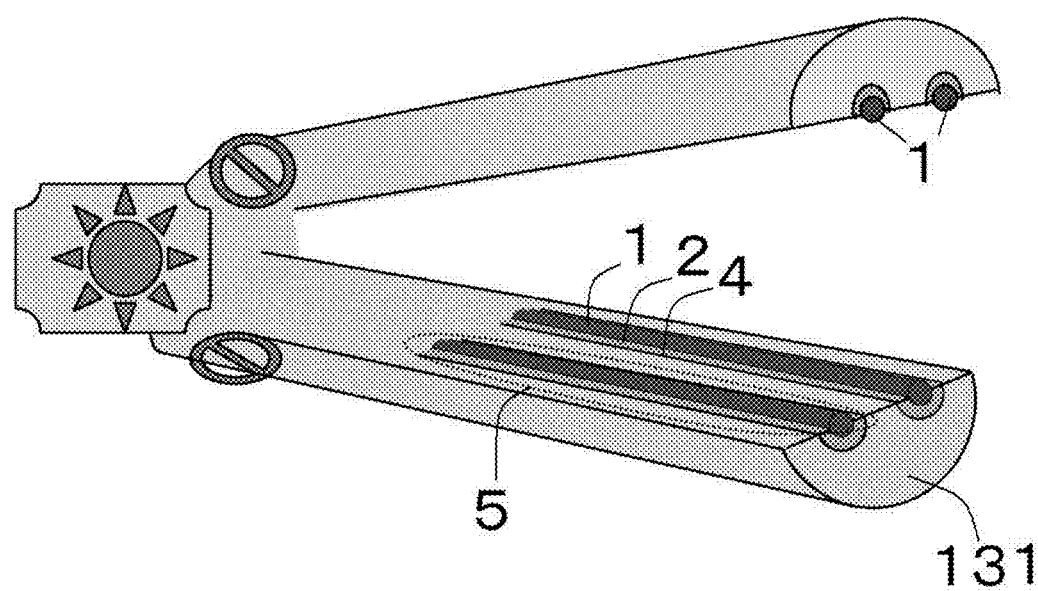

[Fig.18]
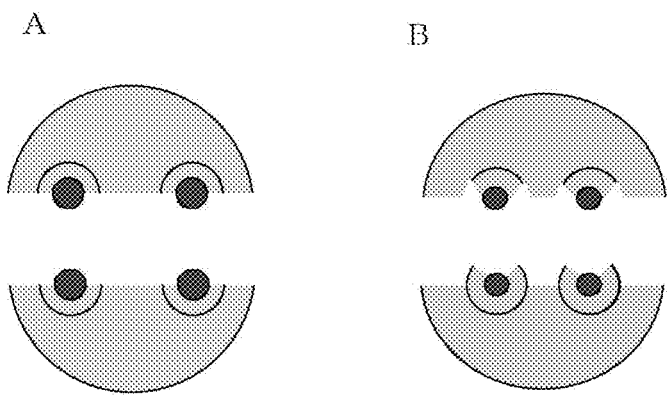
[Fig.19]
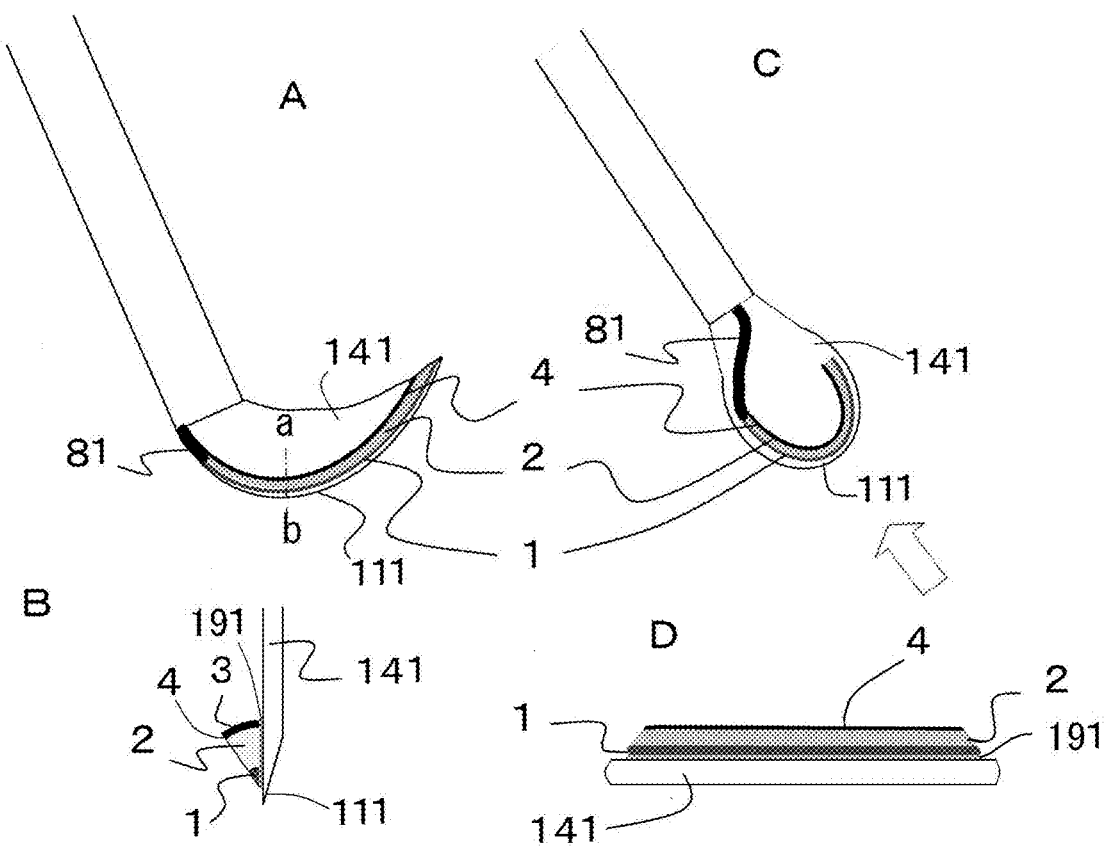

[Fig.20]
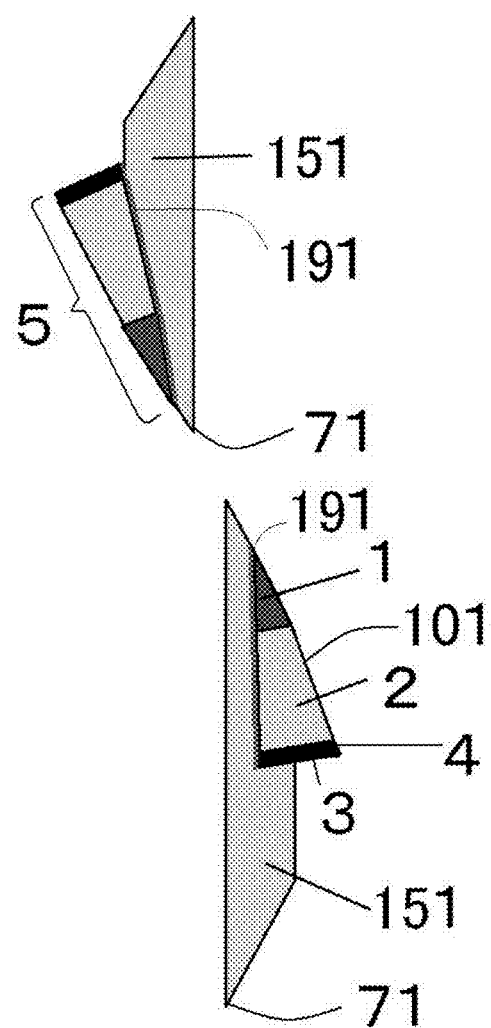

[Fig.21]
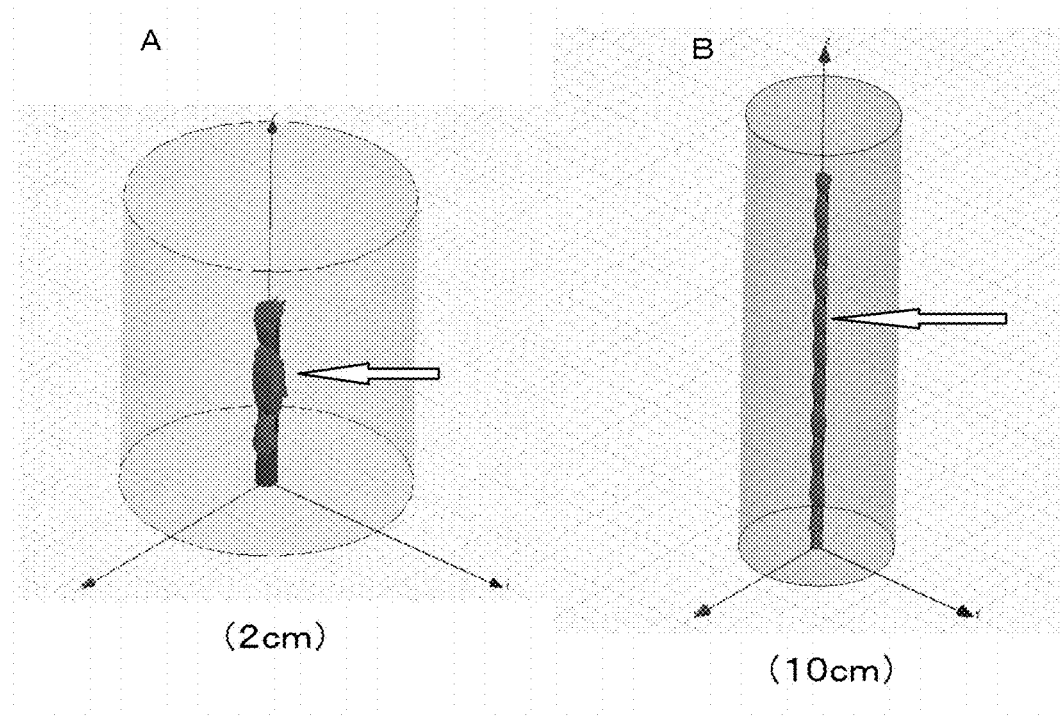
[Fig.22]
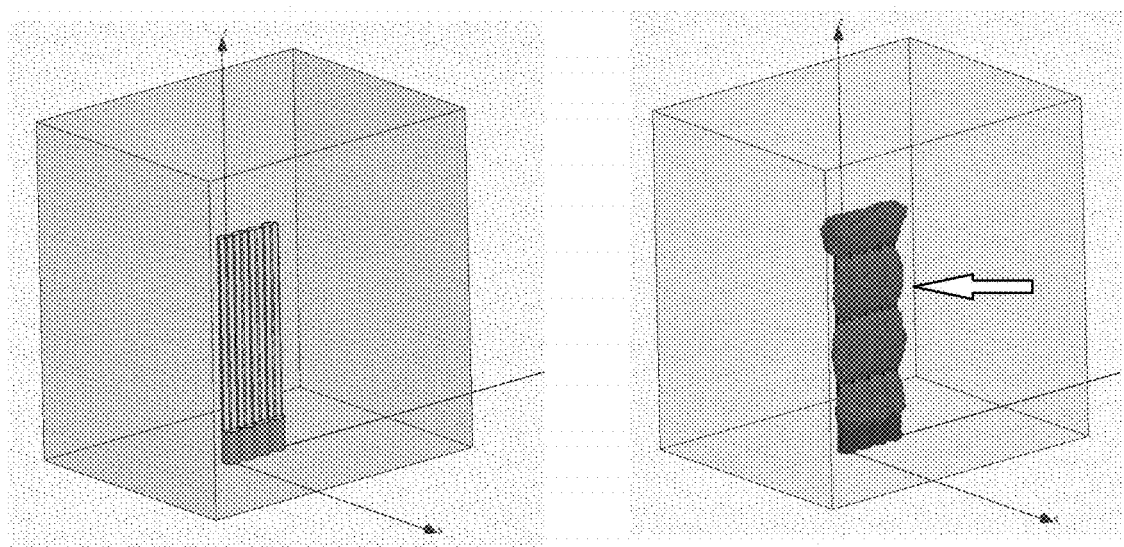

[Fig.23]
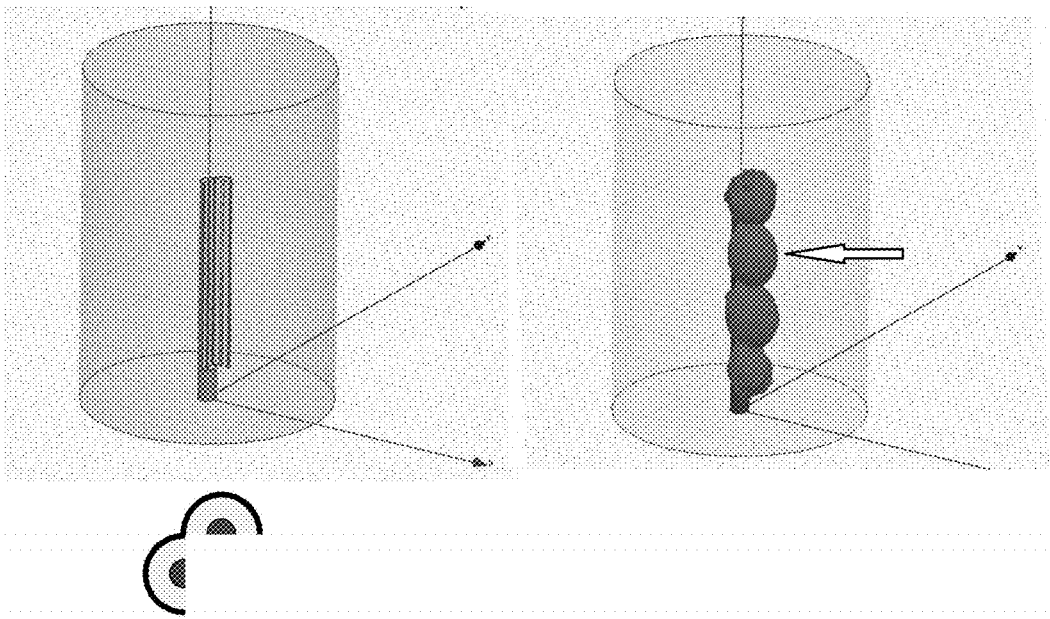
[Fig.24]
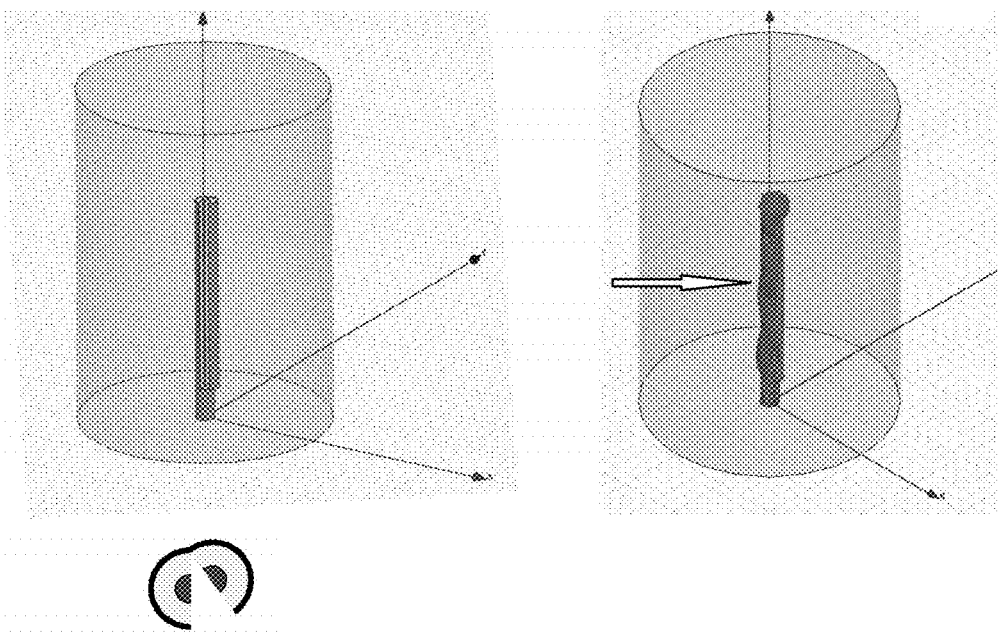

[Fig.25]
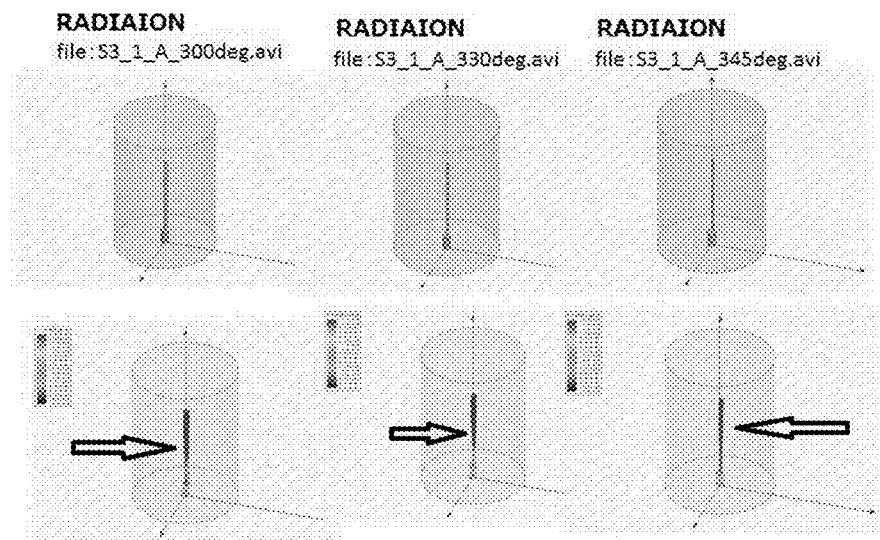

MICROWAVE SURGICAL INSTRUMENT

TECHNICAL FIELD

The present invention relates to a microwave surgical instrument.

The present application claims priority from Japanese Patent Application Nos. 2011-174602 and 2011-180042 which are incorporated herein by reference.

BACKGROUND ART

Microwaves are known to be able to coagulate (fix) biological tissues such as the digestive organ, liver, bladder, prostate gland, uterus, blood vessel, and intestine at low temperature and have been used for a surgical treatment device.

In the case of using a conventional electric cautery or the like, the surface of a biological tissue is heated and coagulated with Joule heat using a high-frequency voltage mainly at a frequency of 500 kHz. In coagulation by the conventional electric cautery or the like using Joule heat, a biological tissue is easily carbonized and coagulated, and hence the coagulated surface is dissected and comes off from the biological tissue in some cases.

In contrast, when microwaves are applied to a biological tissue, the microwaves excite intercellular water molecules uniformly irrespective of depth to cause heat generation. This dielectric heat evaporates moisture in the biological tissue, thereby coagulating (immobilizing) the biological tissue.

The use of microwaves enables a biological tissue to be coagulated at relatively low temperature (100° C. or less). Therefore, the biological tissue can be kept in a fixed state in which the function of the biological tissue is suspended while the cell shape of the biological tissue is maintained.

Therefore, the coagulated surface can be prevented from being dissected and coming off from the biological tissue after treatment.

The inventors of the present invention invented a microwave surgical instrument having a halved structure of a coaxial cable as an instrument for performing coagulation and hemostasis of a biological tissue through use of microwaves and filed a patent application thereof (Patent Literature 1).

Further, besides high-frequency waves, ultrasonic waves are the only energy device capable of cutting a tissue without causing bleeding. However, the inventors of the present invention have developed a device which has a higher sealing force and higher hemostasis performance than those of high-frequency waves and ultrasonic waves, through use of microwaves.

The inventors of the present invention filed a patent application of a device which includes a blade, an insulator, and an external conductor directly connected to a central conductor of a coaxial cable for transmitting microwaves, in which a blade edge is exposed from the external conductor (Patent Literature 2).

Microwaves can coagulate and fix a biological tissue and perform hemostasis of a bleeding region, and further can close (seal) a vessel structure such as a blood vessel or a lymph vessel before incision and excision, thereby enabling an operation in which bleeding and emigration are minimized.

CITATION LIST

Patent Literature

[PTL 1] JP 2008-54926 A
[PTL 2] JP 2008-54925 A

SUMMARY OF INVENTION

Technical Problem

The present invention mainly has two objects.
(Object 1)

In a related-art microwave surgical instrument, a diameter of a general coaxial cable is almost the same as that of a tip of the surgical instrument. Therefore, a surgical instrument having a fine tip capable of transmitting microwaves cannot be produced, and hence microwaves cannot be locally applied to a minute biological tissue.

Further, microwaves are attenuated when being transmitted to a thin tip of a surgical instrument, and hence the tip is required to have thickness to some degree so as to sufficiently transmit microwaves to a biological tissue. However, such thickness hinders the flexible movement of the surgical instrument.

Thus, it is an object of the present invention to provide a surgical instrument capable of locally applying microwaves to a minute biological tissue.

(Object 2)

In a microwave surgical instrument having a structure of a coaxial cable, the exposed portion of a central conductor is short, and hence the application of the microwave surgical instrument has been limited. When the exposed portion of the central conductor is short, there is a problem in that a gastrointestinal organ having a large diameter cannot be sealed. Further, when a blade edge portion is long or curved, microwaves cannot be radiated uniformly over a blade edge line during incision.

Thus, it is an object of the present invention to provide a surgical instrument capable of radiating microwaves uniformly over a blade edge line.

Solution to Problem

The inventors of the present invention have earnestly studied so as to achieve Object 1 described above, and as a result, found that microwaves can be transmitted to a tip of a coaxial body which is tapered (hereinafter sometimes referred to as "tapered coaxial body") and that microwaves are radiated from the entire central conductor exposed in a major axis direction by decreasing a sectional area (preferably diameter) of a central conductor and a sectional area (preferably inner diameter) of an external conductor gradually or in a step-by-step manner with a ratio between the sectional area (diameter) of the central conductor and the sectional area (inner diameter) of the external conductor being set to be constant, thereby achieving the present invention (microwave surgical instrument including a tapered coaxial body).

Further, the inventors of the present invention have earnestly studied so as to achieve Object 2 described above, and as a result, found that, when a surgical instrument includes an elongated biological tissue contact section in which a central conductor directly or indirectly connected to an internal conductor of a coaxial cable is exposed long in a major axis direction, a coagulation and sealing force becomes strong, a tissue can be fixed in a line shape, and a vertically long coagulated region can be achieved even in a curve, thereby achieving the present invention (microwave surgical instrument including a central conductor exposed long).

Note that, microwaves can coagulate a biological tissue at relatively low temperature (100° C. or less) and can suspend the function of the biological tissue to keep it in a fixed state while maintaining the cell shape of the biological tissue.

That is, the present invention includes the following embodiments.

1. A microwave surgical instrument, including:
    a microwave transmitting section; and
    a coaxial body,
    in which the microwave transmitting section includes a coaxial cable including an internal conductor,
    in which the coaxial body includes a central conductor connected to the microwave transmitting section and the internal conductor, an insulator covering a part or a whole of the central conductor, and an external conductor covering a part or a whole of the insulator, and the coaxial body further includes a biological tissue contact section including the central conductor that is not partially covered with the insulator and the external conductor and is exposed in a major axis direction, and
    in which a sectional area of a tip of the coaxial body is smaller than a sectional area of a portion connected to the microwave transmitting section conduction of the coaxial body.

2. A microwave surgical instrument according to Item 1, in which a sectional shape of the central conductor of the tip of the coaxial body and a sectional shape of the external conductor of the tip of the coaxial body are circular shapes.

3. A microwave surgical instrument according to Item 2, in which a ratio between a diameter of the central conductor of the tip of the coaxial body and a diameter of the central conductor of the portion connected to the microwave transmitting section is substantially the same as a ratio between an inner diameter of the external conductor of the tip of the coaxial body and an inner diameter of the external conductor of the portion connected to the microwave transmitting section.

4. A microwave surgical instrument according to any one of Items 1 to 3, further including a support for supporting the coaxial body,
    in which the biological tissue contact section of the coaxial body includes the central conductor exposed long, an insulator surface provided on each of both sides of the central conductor, and an external conductor end substantially parallel to the central conductor, the external conductor end being provided on an outer side of the insulator surface.

5. A microwave surgical instrument according to any one of Items 1 to 4, in which the biological tissue contact section includes a plurality of biological tissue contact sections.

6. A microwave surgical instrument according to Item 5, in which the plurality of biological tissue contact sections include two opposed biological tissue contact sections.

7. A microwave surgical instrument according to any one of Items 1 to 6, in which the biological tissue contact section includes two insulator surfaces forming a reflex angle or a minor angle.

8. A microwave surgical instrument according to Item 6 or 7, in which the microwave surgical instrument includes a tweezers-type instrument.

9. A microwave surgical instrument according to any one of Items 1 to 8, further including a pull-in tube for storing the microwave transmitting section,
    in which the biological tissue contact section is capable of being pulled in and out of the pull-in tube.

10. A microwave surgical instrument according to Item 9, in which tips of two biological tissue contact sections are directly or indirectly connected to each other.

11. A microwave surgical instrument according to Item 10, in which the tips of the two biological tissue contact sections are connected to each other via a wire.

12. A microwave surgical instrument according to any one of Items 2 to 11, in which the tip of the coaxial body has a diameter of 0.2 to 1.5 mm.

13. A microwave surgical instrument according to any one of Items 2 to 12, in which a ratio of a diameter of the central conductor with respect to an inner diameter of the external conductor is 0.2 to 0.4.

14. A microwave surgical instrument according to any one of Items 1 to 13, in which the coaxial body has a length of 1 to 80 mm.

15. A microwave surgical instrument according to any one of Items 1 to 14, in which the biological tissue contact section has a length of 1 to 40 mm.

16. A microwave surgical instrument, including:
    a microwave transmitting section including a coaxial cable including an internal conductor;
    a coaxial body including a central conductor connected to the microwave transmitting section and connected to the internal conductor, an insulator covering a part or a whole of the central conductor, and an external conductor covering a part or a whole of the insulator; and
    a support for supporting the coaxial body,
    in which the coaxial body includes a biological tissue contact section including the central conductor exposed long, an insulator surface provided on each of both sides of the central conductor, and an external conductor end substantially parallel to the central conductor, the external conductor end being provided on an outer side of the insulator surface.

17. A microwave surgical instrument according to Item 16, in which the biological tissue contact section includes two insulator surfaces forming a reflex angle or a minor angle.

18. A microwave surgical instrument according to Item 16 or 17, in which a ratio between a diameter of the central conductor of a tip of the coaxial body and a diameter of the central conductor of a portion connected to the microwave transmitting section of the coaxial body is substantially the same as a ratio between an inner diameter of the external conductor of the tip of the coaxial body and an inner diameter of the external conductor of the portion connected to the microwave transmitting section.

19. A microwave surgical instrument according to any one of Items 16 to 18, in which the biological tissue contact section includes a plurality of biological tissue contact sections.

20. A microwave surgical instrument according to Item 19, in which the plurality of biological tissue contact sections are juxtaposed to each other.

21. A microwave surgical instrument according to Item 20, in which the plurality of biological tissue contact sections juxtaposed to each other are opposed to each other.

22. A microwave surgical instrument according to Item 19, in which the plurality of biological tissue contact sections include two biological tissue contact sections opposed to each other.

23. A microwave surgical instrument according to Item 21 or 22, in which the plurality of biological tissue contact sections include a biological tissue contact section in which an angle formed by insulator surfaces is a minor angle and a biological tissue contact section in which the angle formed by insulator surfaces is a reflex angle, the biological tissue contact sections being opposed to each other.
24. A microwave surgical instrument according to any one of Items 21 to 23, in which the microwave surgical instrument includes a sealing unit for a biological tissue.
25. A microwave surgical instrument according to Item 16, further including a jaw opposed to the biological tissue contact section in which an angle formed by two insulator surfaces is 270° or more.
26. A microwave surgical instrument according to Item 16, in which the biological tissue contact section includes two biological tissue contact sections having external conductor ends that are connected to each other, the two biological tissue contact sections being opposed to each other at an angle.
27. A microwave surgical instrument according to Item 16, in which the support includes a surgical instrument for cutting, incision, excision, or dissect, and the coaxial body is provided closely to and substantially in parallel with an edge or a blade edge line of the surgical instrument.
28. A microwave surgical instrument according to Item 27, in which the biological tissue contact section of the coaxial body includes two insulator surfaces forming an acute angle.
29. A microwave surgical instrument according to Item 27 or 28, in which one insulator surface forming the biological tissue contact section adheres to the surgical instrument for cutting, incision, excision, or dissect.
30. A microwave surgical instrument according to any one of Items 26 to 29, in which the microwave surgical instrument for cutting, incision, excision, or dissect includes any one of a dissector, scissors, and a surgical blade.
31. A microwave surgical instrument according to any one of Items 16 to 30, in which the biological tissue contact section has a length of 5 mm or more and 150 mm or less.

Advantageous Effects of Invention (Microwave Surgical Instrument Including Tapered Coaxial Body)

In general, when a coaxial cable becomes thin, the electric power of microwaves that can be transmitted decreases. However, the microwave surgical instrument including a tapered coaxial body of the present invention can transmit microwaves while minimizing a loss of the microwaves up to the vicinity of a tip by setting the tip in a tapered shape (taper). That is, according to the present invention, microwaves can be transmitted to a more minute tip of a surgical instrument. Further, the surgical instrument is capable of being curved flexibly and moving in the same way as in a high-frequency wire capable of coagulating a tissue in an entire wire.

Specifically, a central conductor exposed in a major axis direction, which is positioned at the tip of the tapered coaxial body, can radiate microwaves from the entire central conductor, and thus a minute tip of the exposed central conductor can also radiate microwaves. As is apparent from FIG. 11, it was confirmed that the mesenteriolum can be coagulated in accordance with its shape through use of the microwave surgical instrument of the present invention.

The surgical instrument of the present invention has a remarkably thin tip which enables delicate treatment required for an operation. The local treatment by the remarkably thin tip enables coagulation and hemostasis of a minute biological tissue without damaging a neighboring tissue. Delicate treatment and local treatment are very important for a brain surgery.

For example, a tweezers-type surgical instrument holds and crushes only an intended fine biological tissue structure, thereby performing hemostasis, coagulation, fixation, and/or sealing. Further, a pen-type surgical instrument can be brought into contact with a fine bleeding region for hemostasis.

Further, minute microwave transmitting means increases the possibility of the development of a novel surgical instrument. For example, tips of two biological tissue contact sections are connected to each other to form a ring structure or horns arranged in parallel; then, a root of a polypous tissue is removed after being coagulated and fixed. In this manner, a non-bleeding band with a width of the horn can be created, with the result that a polyp tissue can be removed without causing bleeding and the mucosa and the like can be coagulated.

Further, treatment can be performed with small electric power and high safety.

(Microwave Surgical Instrument Including Central Conductor Exposed Long)

A surgical instrument including a central conductor exposed long of the present invention can radiate microwaves uniformly from the entire central conductor exposed long and can form a coagulation line which is long and uniform or a long sealing line in a biological tissue. Further, a long incised wound involving a coagulation line can be formed. The formation of a coagulation line or a sealing line can minimize bleeding in treatment such as cutting, incision, excision, and dissect.

Further, the surgical instrument of the present invention is a surgical instrument which is unlikely to damage a neighboring tissue. Further, the surgical instrument of the present invention enables treatment with small electric power and high safety.

The biological tissue contact section of the present invention, in which an angle formed by two insulator surfaces is a reflex angle or a minor angle, can easily position a biological tissue, and hence enables a delicate operation to achieve correct coagulation and fixation.

The surgical instrument of the present invention, in which the plurality of biological tissue contact sections are provided so as to be opposed to each other, can grip a biological tissue to seal the biological tissue. In particular, the surgical instrument of the present invention capable of forming a long sealing line can achieve sealing of a gastrointestinal organ (for example, intestinal tract) having a large diameter at the first trial.

The surgical instrument of the present invention, in which the biological tissue contact section having a reflex angle and the biological tissue contact section having a minor angle are provided so as to be opposed to each other, can crush a tissue in the opposed directions and can radiate microwaves to the tissue while applying a strong pressure to a holding section, thereby achieving strong sealing. Further, the surgical instrument facilitates positioning and gripping and facilitates the approach of the central conductors and the approach of the external conductors without misalignment to suppress the generation of sparks.

The surgical instrument of the present invention, in which the biological tissue contact sections are juxtaposed in contact with each other, can apply microwaves to a region having length and width. By adjusting the length and the number of coaxial bodies, a desired coagulated region or sealing region can be formed. The surgical instrument in which the biological tissue contact sections are juxtaposed at a distance can form a plurality of sealing lines.

The surgical instrument of the present invention, in which the plurality of biological tissue contact sections juxtaposed to each other are provided so as to be opposed to each other, form a wide sealing region or a plurality of sealing lines at a time by gripping a biological tissue with the plurality of biological tissue contact sections. When a region between the plurality of sealing lines or the wide sealing region is cut and excised, a margin is sealed, with the result that cutting and excision can be performed without causing bleeding.

Further, in the plurality of biological tissue contact sections of the present invention, microwaves in phase are radiated, and thus the microwaves can be radiated to a tissue from a plurality of directions additively and efficiently without interfering with each other.

Further, the surgical instrument of the present invention, in which the coaxial body adheres to the surgical instrument for cutting, incision, excision, or dissect, and the exposed central conductor is provided closely to and substantially in parallel with the blade edge line or the edge of the surgical instrument, can form a long coagulation line in the wound by applying microwaves to a biological tissue immediately before treatment such as cutting, incision, excision, and dissect and during the treatment thereof while keeping the function of a surgical blade. The surgical instrument can radiate microwaves uniformly over the entire blade edge line even in the case where the blade edge line is long or curved. Then, treatment such as cutting, incision, excision, and dissect can be performed without causing bleeding or with a small amount of bleeding.

The surgical instrument of the present invention can be held and used in the same way as in each of the conventionally-used surgical instruments. Further, the biological tissue contact section of the present invention can be combined with a great number of medical instruments by being formed small and thin in accordance with a surgical instrument to be applied.

BRIEF DESCRIPTION OF DRAWINGS

FIG. 1 A view illustrating side surfaces of a tip of a microwave transmitting section and a tapered coaxial body.

FIGS. 2 Views illustrating a tapered coaxial body including a biological tissue contact section. (A) is a top view; (B) is a side view; (C) is a sectional view in an axial direction; (D) is a sectional view in a coaxial cable connecting section, in which $a_1$ represents a diameter of a central conductor and $b_1$ represents an inner diameter of an external conductor. (E) is an end view of the tip, in which $a_2$ represents a diameter of the central conductor and $b_2$ represents an inner diameter of the external conductor.

FIG. 3 A perspective view of a tweezers-type surgical instrument including two biological tissue contact sections.

FIGS. 4 Views illustrating an instrument having a ring-shaped structure in which tips of two biological tissue contact sections are connected to each other. (A) illustrates a state in which the ring is largest; and (B) illustrates a state in which the ring is being pulled in a pull-in tube.

FIG. 5 A sectional view in an axial direction of a surgical instrument in the state of B of FIG. 4.

FIG. 6 A view illustrating a surgical instrument of the present invention including two biological tissue contact sections capable of being pulled in.

FIGS. 7 Views illustrating a production example of a tapered coaxial body of the present invention.

FIGS. 8 Microwave radiation analysis views from a biological tissue contact section (length: 2 cm) in which an angle formed by two insulator surfaces is 180°. Microwave radiation was analyzed in seawater at a microwave frequency of 2,450 MHz through use of a high-frequency three-dimensional electromagnetic field simulator having a coaxial structure with an outer diameter of 2.8 mm. A portion indicated by an arrow corresponds to a microwave radiation region. It was verified that microwaves were radiated up to a tip of the tapered coaxial body.

FIG. 9 Microwave radiation analysis views from a biological tissue contact section (length: 5 cm) in which an angle formed by two insulator surfaces is 180°. Microwave radiation was analyzed in seawater at a microwave frequency of 2,450 MHz through use of a high-frequency three-dimensional electromagnetic field simulator having a coaxial structure with an outer diameter of 2.8 mm. A portion indicated by an arrow corresponds to a microwave radiation region. It was verified that microwaves were radiated up to a tip of the tapered coaxial body.

FIG. 10 Microwave radiation analysis views from biological tissue contact sections (length: 4 cm, 6 cm, 8 cm) in which an angle formed by two insulator surfaces is 180°. Microwave radiation was analyzed in seawater at a microwave frequency of 2,450 MHz through use of a high-frequency three-dimensional electromagnetic field simulator having a coaxial structure with an outer diameter of 2.8 mm. It was verified that microwaves were radiated up to a tip even in the case of the biological tissue contact section having a length of 8 cm.

FIG. 11 It was confirmed that the mesenteriolum can be coagulated in accordance with its shape through use of the microwave surgical instrument of the present invention.

FIGS. 12 (A) is a sectional view of a coaxial body including a biological tissue contact section in which an angle of insulator side formed by two insulator surfaces is a minor angle. (B) is a sectional view of a coaxial body including a biological tissue contact section in which an angle of insulator side formed by two insulator surfaces is a reflex angle.

FIGS. 13 Views illustrating a surgical instrument including a coaxial body having a biological tissue contact section in which an angle of insulator side formed by a tip of a microwave transmitting section and two insulator surfaces is an acute angle. (A) is a top view; (B) is a side view; (C) is a sectional view in a major axis direction; (D) is a sectional view of the microwave transmitting section; and (E) is a sectional view of the coaxial body.

FIGS. 14 Views illustrating a surgical instrument including a coaxial body having a biological tissue contact section in which an angle of insulator side formed by a tip of a microwave transmitting section and two insulator surfaces is a reflex angle. (A) is a top view; (B) is a side view; (C) is a sectional view in an axis direction; (D) is a sectional view of the microwave transmitting section; and (E) is a sectional view of the coaxial body.

FIG. 15 A perspective view of a coaxial body including a biological tissue contact section in which an angle formed by two insulator surfaces is 180°. In FIG. 15, the biological tissue contact section serves as an upper surface of the coaxial body.

FIG. 16 A view illustrating an intestinal tract sealing unit. Jaws each including a plurality of (two) biological tissue contact sections arranged in parallel at a slight distance are provided so as to be opposed to each other.

FIG. 17 An enlarged view of a jaw section of the intestinal tract sealing unit.

FIGS. 18 Sectional views of jaws of the intestinal tract sealing unit. (A) is a sectional view of the jaws each including biological tissue contact sections in which an angle of insulator side formed by two insulator surfaces is 180°. (B) is a sectional view of the jaws where a biological tissue contact section in which an angle of insulator side formed by two insulator surfaces is a minor angle and a biological tissue contact section in which an angle of insulator side formed by two insulator surfaces is a reflex angle are provided so as to be opposed to each other.

FIGS. 19 Views illustrating a hook-type dissector (A) and a rice paddle-type dissector (C) to which a coaxial body exposed at an acute angle along a blade edge line adheres. (B) is an a-b sectional view of the hook-type dissector (A); and (D) is a view of a rice paddle-type dissector (C) when viewed in an arrow direction.

FIG. 20 A sectional view of a blade section (opened state) of medical scissors.

FIGS. 21 Microwave radiation analysis views from biological tissue contact sections in which an angle formed by two insulator surfaces is 180°. In (A), a central conductor is exposed by 2 cm, and in (B), a central conductor is exposed by 10 cm. The microwave radiation was analyzed in seawater at a microwave frequency of 2,450 MHz through use of a high-frequency three-dimensional electromagnetic field simulator having a coaxial structure with an outer diameter of 2.8 mm. A portion indicated by an arrow corresponds to a microwave radiation region. It was verified by electromagnetic wave analysis that microwaves were radiated uniformly despite the length of an exposed portion (vertical division portion) in a major axis vertical division structure.

FIG. 22 Microwave radiation analysis views in the case where four biological tissue contact sections, in which an angle formed by two insulator surfaces is 180°, are juxtaposed to each other. The microwave radiation was analyzed in seawater at a microwave frequency of 2,450 MHz through use of a high-frequency three-dimensional electromagnetic field simulator having a coaxial structure with an outer diameter of 2.8 mm. A portion indicated by an arrow corresponds to a microwave radiation region.

FIG. 23 Views illustrating simulation of a surgical instrument in which two biological tissue contact sections whose external conductor ends are connected to each other are provided so as to be opposed to each other at an angle of 90°. FIG. 23 illustrates that microwaves are added from a right-angle direction to enable efficient radiation. Microwave radiation was analyzed in seawater at a microwave frequency of 2,450 MHz through use of a high-frequency three-dimensional electromagnetic field simulator having a coaxial structure with an outer diameter of 2.8 mm. A portion indicated by an arrow corresponds to a microwave radiation region.

FIG. 24 Views illustrating simulation of a surgical instrument in which two biological tissue contact sections whose external conductor ends are connected to each other are provided so as to be opposed to each other at an angle of 30°. FIG. 24 illustrates that microwaves are radiated to a portion at an acute angle of 30°. Microwave radiation was analyzed in seawater at a microwave frequency of 2,450 MHz through use of a high-frequency three-dimensional electromagnetic field simulator having a coaxial structure with an outer diameter of 2.8 mm. A portion indicated by an arrow corresponds to a microwave radiation region.

FIG. 25 Views illustrating simulation of a surgical instrument in which two biological tissue contact sections whose external conductor ends are connected to each other are provided so as to be opposed to each other at an angle of 60°, 30°, or 15°. Microwave radiation was analyzed in seawater at a microwave frequency of 2,450 MHz through use of a high-frequency three-dimensional electromagnetic field simulator having a coaxial structure with an outer diameter of 2.8 mm. A portion indicated by an arrow corresponds to a microwave radiation region. It was verified that microwaves were radiated over full length up to a tip even at a residual angle of 15°.

DESCRIPTION OF EMBODIMENTS

A microwave surgical instrument including a tapered coaxial body and a microwave surgical instrument including a central conductor exposed long of the present invention are described hereinafter with reference to the drawings. Note that, the present invention is not limited to the surgical instruments illustrated in the drawings.

(Microwave Surgical Instrument Including Tapered Coaxial Body)

A microwave surgical instrument including a tapered coaxial body of the present invention includes a microwave transmitting section including a coaxial cable and a tapered coaxial body. The microwave transmitting section includes a coaxial cable in which an internal conductor, an insulator, and an external conductor are provided coaxially. In the present invention, microwaves at a frequency of 900 to 6,000 MHz can be used equally. The microwave frequency is preferably 2,450±50 MHz. The preferred diameter of the coaxial body is 0.3 to 5.0 mm.

The tapered coaxial body is directly or indirectly connected to the tip of the microwave transmitting section. The sectional area of the tip of the tapered coaxial body (right side of FIG. 1) is smaller than that of a coaxial cable connecting section. The central conductor of the tapered coaxial body is connected to the internal conductor of the coaxial cable or integrally formed therewith.

It is preferred that apart or a whole of the central conductor be covered with an insulator, a part or a whole of the insulator be covered with the external conductor, and a ratio between the sectional area of the central conductor and the sectional area of the external conductor be kept constant. As long as the ratio is kept constant, the coaxial body may become thin gradually or in a step-by-step manner. The tapered coaxial body includes a coaxial body in which a tapered tip keeps a predetermined diameter.

Note that, the shape of each cross-section of the central conductor and the external conductor can be a circular shape, a fan shape, a rectangular shape, a triangular shape, or the like without being particularly limited, and is preferably a circular shape.

In addition, the sectional area of the external conductor generally means a difference between the sectional area of the coaxial cable and the sectional area of the central conductor and the insulator.

A ratio of the circular diameter of the central conductor with respect to the circular inner diameter of the external conductor is preferably 0.2 to 0.4, more preferably 0.22 to 0.3.

The length of the tapered coaxial body is preferably 1 to 80 mm, more preferably 10 to 70 mm, still more preferably 15 to 40 mm.

The diameter of the coaxial cable connecting section of the tapered coaxial body is almost the same as the diameter of the coaxial cable. The diameter of the tip of the tapered coaxial body is 0.2 to 1.5 mm, preferably 0.3 to 1 mm.

The tapered coaxial body includes a biological tissue contact section. In the biological tissue contact section, the central conductor and the external conductor end are exposed, and an insulator is disposed between the central conductor and the external conductor end. That is, the biological tissue contact section includes the central conductor exposed linearly in a major axis direction, insulator surfaces on both sides of the central conductor, and the external conductor end on an outer side of the insulator surfaces. The biological tissue contact section and a biological tissue come into direct contact with each other, and microwaves are directly applied to the biological tissue from the entire exposed central conductor, with the result that the applied microwaves flow through the external conductor at a close position.

A basic structure of the biological tissue contact section is an exposed portion in which a part of the insulator and the external conductor is removed and the central conductor is exposed in a major axis direction of the tapered coaxial body. The central conductor is exposed linearly at the center of the biological tissue contact section, and the insulator is provided on both sides thereof and the external conductor end is provided on an outer side thereof. An angle (see "14" of FIG. 2E) formed by two insulator surfaces present on both sides of the central conductor may be in a range of several degrees to 350°, preferably 10° to 300°, more preferably 15° to 270°. In general, the angle is 180° (see FIG. 2E).

The length of the biological tissue contact section is preferably 1 to 40 mm, more preferably 5 to 35 mm, still more preferably 10 to 30 mm. The length of the exposed central conductor is preferably 1 to 40 mm, more preferably 5 to 35 mm, still more preferably 10 to 30 mm.

Microwaves are radiated from the entire central conductor of the biological tissue contact section, and thereby hemostasis, coagulation, fixation, and/or sealing of a biological tissue in a narrow region can be performed.

The microwave surgical instrument including a tapered coaxial body of the present invention preferably includes a plurality of biological tissue contact sections. In particular, there is given a surgical instrument which allows two biological tissue contact sections to be opposed to each other to grip a biological tissue. The microwave surgical instrument may include a plurality of two sets of opposed biological tissue contact sections.

As a typical instrument, there is given a tweezers-type instrument (FIG. 3). Hemostasis and coagulation of a biological tissue can be performed by gripping the biological tissue with two biological tissue contact sections, and in addition biological tissues which are positioned at a distance can be coagulated simultaneously while being pressed. Therefore, sealing of the tissue can be achieved. Further, by radiating microwaves simultaneously from the two biological tissue contact sections, hemostasis, coagulation, fixation, and/or sealing of a tissue can be performed efficiently. In particular, the microwave surgical instrument including a tapered coaxial body of the present invention enables sealing of a minute tissue.

In biological tissue contact surfaces of a surgical instrument for gripping a biological tissue, an angle of insulator side formed by two insulator surfaces present on both sides of the central conductor may also be in a range of several degrees to 350°, preferably 10° to 300°, more preferably 15° to 27°. In general, the angle is 180° (FIG. 2E). When one of the biological tissue contact sections has a reflex angle (angle larger than 180°) and the other has a minor angle (angle smaller than 180°), a biological tissue can be gripped easily. The biological tissue contact section having a minor angle can easily identify an intended sealing portion, and thus an intended portion can be gripped without misalignment, which enables a delicate operation.

Further, the central conductors and the external conductors of the biological tissue contact sections opposed to each other can respectively brought close to each other easily via a biological tissue. Thus, microwaves can be applied efficiently to the biological tissue, and the generation of sparks caused by the approach between the central conductor and the external conductor can be prevented. A minor angle is 30° to 170°, preferably 60° to 135°, still more preferably 80° to 120°. A reflex angle is 190° to 330°, preferably 225° to 300°, more preferably 240° to 280°.

One or a plurality of coaxial cables for transmission may be provided in a surgical instrument including a plurality of biological tissue contact sections; however, in order to prevent microwaves from interfering with each other, it is preferred that the number of coaxial cables be set so that microwaves in phase can be radiated. A structure in which one coaxial cable for transmission is branched is preferred because microwaves in phase can be radiated.

In the microwave surgical instrument including a tapered coaxial body of the present invention, tips of two opposed biological tissue contact sections may be apart from each other or may be directly or indirectly connected to each other to form a ring. The ring structure enables hemostasis, coagulation, fixation, and/or sealing of a root of a polypous biological tissue (FIG. 4A).

Tips of two biological tissue contact sections are connected to each other directly or indirectly with a wire or the like to form a ring. The wire or the like is not limited, and may be an insulator or a conductor. A transmitting section including a coaxial cable is covered with a pull-in tube and is connected to the tapered coaxial body (FIG. 5). The biological tissue contact section can be pulled in and out of the pull-in tube. A polypous tissue is taken in the ring, and the biological tissue contact section is pulled in the pull-in tube while microwaves are being radiated to the tissue gradually, whereby the root of the polyp is coagulated. After the root of the polyp is coagulated, the ring inner diameter becomes minimum, with the result that the polypous tissue is excised. Further, cutting means may be provided in the pull-in tube.

The microwave surgical instrument including a tapered coaxial body of the present invention includes a surgical instrument in which tips of two opposed biological tissue contact sections are provided so as to be close to each other compared to other sites (FIG. 6). Preferably, the surgical instrument includes a pull-in tube and pull-in means for the pull-in tube. A biological tissue is gripped by two opposed biological tissue contact sections, and the biological tissue is pulled in the pull-in tube, with the result that hemostasis, coagulation, fixation, and/or sealing of a region which is held in contact with the biological tissue contact sections can be performed. In particular, the surgical instrument serves as an endoscope or intravascular forceps to grip a small range of a tissue or coagulate the periphery thereof.

The coaxial cable used in the present invention is connected to a microwave generation device directly or indirectly (via another coaxial cable). The microwave surgical instrument including a tapered coaxial body of the present invention can be inserted in an endoscope and/or a catheter by softening the coaxial cable. The coaxial cable preferably has a holding section made of an insulator so that an operator can hold the holding section during an operation under direct vision such as open abdominal surgery.

The coaxial cable used in the present invention includes a central electrode of a conductive material made of, for example, phosphor bronze, a shield tube of an insulator made of, for example, Teflon (registered trademark) covering the central electrode, and an earth pipe of an external conductor (conductive material) made of, for example, brass. The coaxial cable and an outer side thereof may be covered with a shield holder (also referred to as "guide tube"). It is preferred that the shield holder be formed of a non-conductive member (for example, a non-magnetic coil of Teflon (registered trademark), a fluorine resin, ceramics, or the like).

The microwave surgical instrument including a tapered coaxial body of the present invention enables treatment with small electric power and is also excellent in safety. The electric power to be used in the present invention is 5 W to 100 W, preferably 20 W to 80 W, more preferably 40 W to 60 W. When the electric power is higher than 100 W, the electric power may damage a peripheral tissue. The magnitude of the electric power is adjusted by the length of an exposed portion. Further, when the electric power is less than 5 W, the functions of hemostasis, coagulation, fixation, and sealing may not be sufficient.

Examples of a material for the central conductor of the coaxial body of the present invention include copper, bronze, and aluminum, and examples of a material for the insulator include Teflon (registered trademark) and ceramics. The external conductor is not particularly limited as long as the external conductor is made of a conductive material.

The tapered coaxial body is produced, for example, as follows.

{Formation of Tapered Coaxial Body (FIG. 7A)}

A central conductor is formed by spray forming through use of metal injection molding (MIM). Next, a circumferential surface of the central conductor is coated with an electrically insulative material such as ceramics or a fluorine resin. Alternatively, the central conductor may be formed through use of ceramics injection molding (CIM). An insulation layer can also be formed by coating, drying, and sintering. Further, an external conductor is formed on an upper surface of the insulation layer, for example, through use of the MIM.

{Formation of Biological Tissue Contact Section (FIG. 7B)}

A biological tissue contact section is formed by grinding the tip of the above-mentioned tapered coaxial body (FIG. 7A) with a turning machine or grinding stone.

(Connection to Coaxial Cable)

The tapered coaxial body is electrically and mechanically connected to the microwave transmitting section (FIG. 7C). The tapered coaxial body may be fixed to the microwave transmitting section or removably connected thereto. In a GHz band, an impedance fluctuation caused by the connection can be matched with a circuit.

(Microwave Surgical Instrument Including Central Conductor Exposed Long)

A microwave surgical instrument including a central conductor exposed long of the present invention includes a microwave transmitting section including a coaxial cable including an internal conductor, a coaxial body including a central conductor connected to the internal conductor, an insulator covering a part or a whole of the central conductor, and an external conductor covering a part or a whole of the insulator, and a support for supporting the coaxial body. The microwave transmitting section includes a coaxial cable in which the internal conductor, an insulator, and an external conductor are provided coaxially. In the present invention, although microwaves are not particularly limited, microwaves at a frequency of 900 to 6,000 MHz are preferably used. More preferably, the microwaves at a frequency of 2,450±50 MHz are used. The diameter of the coaxial cable is preferably 2 to 5 mm.

Note that, the shape of each section of the central conductor and the external conductor can be a circular shape, a fan shape, a rectangular shape, a triangular shape, or the like without being particularly limited, and is preferably a circular shape.

In addition, the sectional area of the external conductor generally means a difference between the sectional area of the coaxial cable and the sectional area of the central conductor and the insulator.

The support for supporting the coaxial body is not limited as long as the support can apply a force to the biological tissue contact section provided in the coaxial body. The shape of the support is not limited, and examples thereof include a bar shape, a plate shape, and a cylindrical shape. General surgical instruments such as tweezers, scissors, a surgical blade, and a dissector can be used as a support.

In the surgical instrument including a central conductor exposed long of the present invention, a coaxial body (91) is directly or indirectly provided at a coaxial cable (81) of the microwave transmitting section. The coaxial body is directly or indirectly connected to the internal conductor of the coaxial cable or has a coaxial structure including a central conductor which is an internal conductor itself, an insulator covering the central conductor, and an external conductor covering the insulator. The coaxial body may serve as the coaxial cable itself.

The coaxial body is provided with an elongated biological tissue contact section (5). The biological tissue contact section includes a central conductor (1) connected to the internal conductor of the coaxial cable, which is exposed long in a major axis direction, an external conductor end (4) which is substantially parallel to the exposed central conductor, and an insulator surface (101) between the central conductor and the external conductor end. In the biological tissue contact section, insulator surfaces are formed on both sides with the exposed central conductor being a center line. A basic structure of the biological tissue contact section is an exposed portion formed (by removing a part of the insulator and the external conductor in a vertical direction) with a part of the coaxial body being opened in the vertical direction.

The length of the biological tissue contact section is preferably 3 to 150 mm, more preferably 5 mm to 100 mm, still more preferably 10 mm to 70 mm. In particular, in the case of the tweezers, the length is preferably 5 to 40 mm, and in the case of the intestinal tract sealing unit, the length is preferably 10 to 70 mm.

Microwaves are uniformly radiated from the entire central conductor exposed long in a major axis direction of the biological tissue contact section, and hence microwaves can be applied directly to a biological tissue (FIGS. 21 to 25). The applied microwaves are directed to the external conductor end at a close position and can coagulate and fix a biological tissue at low temperature to form a long and uniform coagulation line or long sealing line.

When the biological tissue contact section is brought close to a biological tissue under the condition that microwaves are being transmitted to the central conductor, the microwaves can start being applied to the biological tissue immediately before the biological tissue contact section is brought into contact with the biological tissue.

The biological tissue contact section includes the insulator surfaces (101) on both sides of the central conductor. An angle (θ of FIG. 12, which is sometimes referred to as "contact section angle") formed by the two insulator surfaces may be a reflex angle or a minor angle. FIG. 12 illustrates a sectional view (A) of a coaxial body in which a contact section angle is a minor angle, and a sectional view (B) of a coaxial body in which the contact section angle is a reflex angle.

In the case where the contact section angle is a reflex angle, the reflex angle is preferably more than 180° and less than 355°. When the contact section angle is 355° or more, microwaves are poorly radiated from the central conductor of the biological tissue contact section to a biological tissue. In the case where the contact section angle is a minor angle, the minor angle is preferably more than 5° and less than 180°.

When the surgical instrument having a contact section angle of a minor angle (FIG. 13) is pressed against a biological tissue, the surgical instrument forms a long coagulation line in the biological tissue and exhibits the effects of coagulation, fixation, and hemostasis. Further, when the surgical instrument having a contact section angle of a minor angle grips a biological tissue together with a biological tissue contact section having a contact section angle of a reflex angle (FIG. 14), the surgical instrument can form a longer sealing line. The support of the surgical instruments of FIGS. 13 and 14 can reinforce the strength of the coaxial body.

Further, a surgical instrument (FIG. 19) in which a coaxial body including a biological tissue contact section having a contact section angle of 60° or less is caused to adhere to a surgical blade or the like can form a coagulation line in a biological tissue to be incised, excised, cut, or dissected.

The surgical instrument including a central conductor exposed long of the present invention preferably includes a plurality of biological tissue contact sections. The plurality of biological tissue contact sections may be connected to internal conductors of coaxial cables branched from one coaxial cable or may be connected to internal conductors of a plurality of coaxial cables. It is preferred that microwaves in phase be applied so that the microwaves do not interfere with each other. This is because microwaves in phase are radiated to a tissue additively and efficiently without interfering with each other. A structure in which one coaxial cable for transmission is branched is preferred because microwaves in phase can be radiated.

The surgical instrument including a central conductor exposed long of the present invention includes a surgical instrument in which a plurality of biological tissue contact sections are juxtaposed to each other. In a surgical instrument in which biological tissue contact sections are arranged in the same direction, the biological tissue contact sections may be juxtaposed in contact with each other (FIG. 22) or provided in parallel at a distance. Sufficient microwave radiation was verified also in high-frequency simulation with 1 mV of microwaves added in the above-mentioned form.

The surgical instrument in which the biological tissue contact sections are juxtaposed in contact with each other can radiate microwaves long and widely with respect to a biological tissue. Microwaves radiated from each biological tissue contact section are in phase and added up without interfering with each other to be radiated to a biological tissue. By adjusting the length of each biological tissue contact section and the number of coaxial bodies, a desired coagulated region or sealed region can be formed. The length of each biological tissue contact section is 15 to 160 mm, and 2 to 10, preferably 3 to 7 biological tissue contact sections are juxtaposed. A preferred width of each biological tissue contact section in this case is 3 to 8 mm.

The surgical instrument in which the biological tissue contact sections are juxtaposed in parallel at a distance can coagulate portions which are disposed away at a time. It is preferred that the biological tissue contact section be provided with unevenness or grooves on a surface so as to prevent slippage.

The surgical instrument including a central conductor exposed long of the present invention includes a surgical instrument including a plurality of opposed biological tissue contact sections. By providing two opposed biological tissue contact sections to an instrument with a crushing structure and applying microwaves to a biological tissue while gripping the biological tissue through use of the instrument, the biological tissue can be coagulated, fixed, and sealed over a long distance. The microwaves radiated from the central conductors of the two biological tissue contact sections are directly applied to the biological tissue and are directed to the external conductor at a close position. Microwaves in phase are simultaneously applied to the biological tissue from the two biological tissue contact sections, with the result that the microwaves are applied to the biological tissue additively and efficiently to achieve sealing without interfering with each other.

In particular, the surgical instrument including a central conductor exposed long of the present invention applies microwaves directly to a biological tissue from the entire long central conductor. Therefore, the surgical instrument can form a long sealing line and can seal even an intestinal tract having a large vessel structure at the first trial.

The surgical instrument including a central conductor exposed long of the present invention includes a surgical instrument in which juxtaposed biological tissue contact sections are opposed to each other. Wide sealing can be achieved or a plurality of sealing lines can be formed at a time by gripping a biological tissue with a plurality of juxtaposed biological tissue contact sections. When a region between a plurality of sealing lines or a wide sealing region is cut and excised, cutting and excision without bleeding can be performed.

Specifically, there is given an intestinal tract sealing unit (FIGS. 16 to 18). Jaws each including two juxtaposed biological tissue contact sections are provided so as to be opposed to each other. The opposed biological tissue contact sections are engaged with each other to grip a biological tissue, and microwaves are applied simultaneously. The length of the biological tissue contact section is preferably 10 to 80 mm, the width of the biological tissue contact section is preferably 1 to 5 mm, and the interval between the biological tissue contact sections is preferably 0.5 to 3 mm. Two sealing lines are formed simultaneously by the applied microwaves. After that, a region between the two sealing lines can be cut or excised without causing bleeding.

In the intestinal tract sealing unit of FIG. 16, two coaxial bodies are set on each jaw so as to be juxtaposed to each other. The jaws are opposed to each other, and the contact section angle of each biological tissue contact section is basically 180°. A total of four coaxial bodies are connected to the coaxial cables branched from one coaxial cable. The length of the coaxial body is 70 mm, the width of the coaxial body is 2 mm, and the distance between the coaxial bodies arranged in parallel is 1 to 2 mm.

In the case where the biological tissue contact sections grip a biological tissue, when one contact section angle is a reflex angle and the other contact section angle is a minor angle, large pressure can be applied and strong sealing can be achieved. Further, the biological tissue contact section having a minor angle can identify an intended sealing portion easily, and hence an intended place can be gripped without misalignment in a horizontal direction, which enables a delicate operation. Further, the central conductors and the external conductors of the opposed biological tissue contact sections are respectively brought close to each other easily via a biological tissue. Thus, microwaves can be applied to a biological tissue efficiently, and the generation of sparks caused by the approach between the central conductor and the external conductor can be prevented. The effect of preventing the generation of sparks is important for a surgical instrument in which a plurality of juxtaposed biological tissue contact sections are opposed to each other.

Further, a jaw surface is preferably provided with unevenness in a horizontal direction because the gripped tissue can be prevented from being slipped out.

A preferred contact section angle varies depending on the surgical instrument. In a preferred contact section angle of the biological tissue contact section of a surgical instrument having a gripping function, a minor angle is 30° to 170°, preferably 60° to 135°, still more preferably 80° to 120°. Further, in the contact section angle, a reflex angle is 190° to 330°, preferably 225° to 300°, still more preferably 240° to 280°.

The present invention also includes a surgical instrument including a biological tissue contact section having a contact section angle of 270° or more and a jaw having no biological tissue contact section, which is opposed to the biological tissue contact section having a contact section of 270° or more. The contact section angle is preferably 270° to 355°, and microwaves are radiated from a narrow open portion in a major axis direction of a coaxial structure. Microwaves can be applied to a biological tissue more efficiently by pressing the biological tissue to a biological tissue contact section with a jaw. The jaw may be an insulator or a conductor such as a metal and may have not only a pressing function but also a cutting function.

The present invention includes a surgical instrument in which two biological tissue contact sections whose external conductor ends are connected to each other are opposed to each other at an angle. FIGS. 23 and 24 illustrate a cross-section of the instrument and the results of high-frequency electromagnetic field simulation of 1 mV. An angle of insulator side formed by the two biological tissue contact sections is a minor angle, preferably an acute angle. Microwaves can be applied to a biological tissue efficiently from a plurality of directions by bringing the biological tissue into contact with an angled portion formed by the biological tissue contact sections. A jaw may be provided so as to be opposed to the two biological tissue contact sections, and microwaves can be applied to the biological tissue efficiently by pressing the biological tissue against the angled portion with the jaw. The jaw may be an insulator or a conductor such as a metal and may have not only a pressing function but also a cutting function.

The surgical instrument including a central conductor exposed long of the present invention includes the following configuration in which a support is a surgical instrument for cutting, incision, excision, or dissect, and a coaxial body is provided closely to and substantially in parallel with an edge of the surgical instrument (FIGS. 19 and 20). In the case where the surgical instrument is an edged tool such as a surgical blade or scissors, the edge of the surgical instrument is a blade edge line. The contact section angle of the biological tissue contact section provided in the coaxial body is an acute angle, preferably 60° or less. The coaxial body is provided so that the exposed central conductor is disposed at a position closest to the edge or the blade edge line of the surgical instrument.

It is preferred that the coaxial body and the support such as a dissector adhere to each other by a method involving causing one insulator surface of the biological tissue contact section to adhere to a treatment section of the support via an insulator or an insulation film.

The contact section angle of the biological tissue contact section to be caused to adhere to a dissector or the like is in a range of 0° to 60°, preferably 10° to 45°, still more preferably 15° to 30°. The coaxial body is provided substantially in parallel with the edge of the surgical instrument.

The cross-section of the coaxial body adhering to the surgical instrument such as a dissector has a fan shape with the central conductor being the center or a substantially triangular shape with the central conductor being a vertex.

The cross-section of the central conductor may be a circular shape or the tip thereof may be pointed.

Examples of a surgical instrument for cutting, incision, excision, or dissect include a dissector, scissors, and a surgical blade. The distance between the edge (blade edge line) and the central conductor is 0.3 mm to 2 mm, preferably 0.5 to 1.5 mm. It is preferred that the support and the insulator surface be connected to each other through adhesion, and the support and the insulator surface are caused to adhere to each other so as not to impair the effects of dissect, cutting, incision, and excision.

The surgical instrument of the present invention applies microwaves to a biological tissue immediately before cutting, incision, excision, and dissect and during the treatment thereof while keeping the functions of cutting, incision, excision, or dissect, forms a long coagulation line in the biological tissue which has been incised or the like, and enables treatment with minimized bleeding.

Further, the surgical instrument of the present invention can be held and used in the same way as in each of the conventionally used surgical instruments. The biological tissue contact section can be combined with a great number of medical instruments by being formed small and/or thin in accordance with a surgical instrument to be applied.

Examples of the material for the central conductor of the coaxial body of the present invention include copper, bronze, and aluminum, and examples of the material for the insulator include Teflon (registered trademark) and ceramics. It is sufficient that the external conductor be made of a conductive material.

The coaxial cable of the microwave transmitting section provided in the present invention is connected to the microwave generation device directly or via a separate coaxial cable, and supplied with microwaves. The surgical instrument including a central conductor exposed long of the present invention can be inserted in an endoscope and/or a catheter by softening the coaxial cable. The surgical instrument including a central conductor exposed long of the present invention preferably has a holding section made of an insulator so that an operator can hold the holding section during an operation under direct vision such as open abdominal surgery.

The coaxial cable used in the present invention includes an internal conductor of a conductive material made of, for example, phosphor bronze, a shield tube of an insulator made of, for example, Teflon (registered trademark) covering the internal electrode, and an earth pipe of an external conductor (conductive material) made of, for example, brass. The coaxial cable and an outer side thereof may be covered with a shield holder (also referred to as "guide tube"). It is preferred that the shield holder be formed of a non-conductive member (for example, a non-magnetic coil of Teflon (registered trademark), phosphor bronze, or the like).

The microwave surgical instrument including a central conductor exposed long of the present invention enables treatment with small electric power and is also excellent in safety. The electric power to be used in the present invention is 5 W to 100 W, preferably 10 W to 80 W, more preferably 20 W to 60 W. When the electric power is higher than 110 W, the electric power may damage a peripheral tissue. The magnitude of the electric power is adjusted by the length of an exposed portion. Further, when the electric power is less than 5 W, the functions of hemostasis, coagulation, fixation, and sealing may not be sufficient.

EXAMPLE (Intestinal Tract Sealing)
An intestinal tract sealing experiment by open abdominal surgery was conducted with respect to a dog having a weight of 8 kg through use of the microwave surgical instrument including a central conductor exposed long of the present invention. The small intestine was sealed by being irradiated with microwaves at an output of 60 W for 18 seconds by the sealing unit of FIG. 16, with the result that the intestinal tract was sealed and an affected area was cut without causing bleeding. That is, the effect of the present invention was confirmed.

INDUSTRIAL APPLICABILITY

The microwave surgical instrument including a tapered coaxial body of the present invention enables sufficient microwave radiation up to a tip of a device in various delicate treatments required for an operation, and enables local coagulation, fixation, hemostasis, and sealing of a fine biological tissue. Further, the minute microwave transmitting means increases the possibility of the development of a novel surgical instrument. Further, the microwave surgical instrument enables treatment with small electric power and high safety. Thus, the microwave surgical instrument has high safety and is excellent in operability in a surgical treatment area in the medical field, in particular, endoscopic treatment in a brain surgery area, an intravascular surgical area, and a gastroenterological area.

Further, the microwave surgical instrument including a central conductor exposed long of the present invention enables provision of various surgical instruments using the characteristics of microwaves. The microwave surgical instrument enables an operation while coagulating and immobilizing a biological tissue and is very useful from the viewpoint that the instrument can minimize bleeding. Further, the microwave surgical instrument enables treatment with small electric power and high safety. Accordingly, the present invention provides a surgical instrument which has high safety and is excellent in operability in a surgical treatment area in the medical field.

REFERENCE SIGNS LIST 1 central conductor
1(a) exposed portion of central conductor
2 insulator
3 external conductor
4 external conductor end
5 biological tissue contact section
6 wire
7 outer cylinder
8 microwave transmitting section (coaxial cable)
9 (tapered) coaxial body
10 pull-in tube
11 internal conductor
12 coaxial cable connecting section (sectional area of portion connected to transmitting section)
13 tip of microwave transmitting section
14 angle formed by two insulator surfaces present on both sides of central conductor
61 blade
71 blade edge line
81 microwave transmitting section (coaxial cable)
91 coaxial body
101 insulator surface
111 edge
121 support
131 support (jaw)
141 support (dissector)
151 support (blade of scissors)
161 connector
171 handle
181 outer cylinder
191 insulation film

The invention claimed is:
1. A microwave surgical instrument comprising:
(a) a microwave transmitting section comprising;
a coaxial cable including an internal conductor;
(b) a coaxial body comprising:
(i) a central conductor connected to said microwave transmitting section and to said internal conductor of said microwave transmitting section,
(ii) an insulator covering a portion of said central conductor,
(iii) an external conductor covering at least a portion of said insulator,
(iv) one or a plurality of biological tissue contact sections comprising:
(A) said central conductor that is exposed in a major axis direction,
(B) said insulator covering non-exposed portion of said central conductor, and
(C) said external conductor; and
(c) a support for supporting said coaxial body,
wherein a diameter of said central conductor at a tip of said coaxial body is smaller than a diameter of said central conductor at said coaxial body that is connected to said microwave transmitting section, and wherein a ratio between the diameter of said central conductor at the tip of said coaxial body and the diameter of said central conductor that is connected to said microwave transmitting section is same as a ratio between an inner diameter of said external conductor at the tip of said coaxial body and an inner diameter of said external conductor at said coaxial body that is connected to said microwave transmitting section.

2. The microwave surgical instrument according to claim 1, wherein said one or a plurality of biological tissue contact sections of element (b)(iv) comprises two opposed biological tissue contact sections.

3. The microwave surgical instrument according to claim 2 further comprising a pull-in tube for storing said microwave transmitting section, wherein at least one of said two opposed biological tissue contact section is configured to be pulled in and out of said pull-in tube and said tips of two said biological tissue contact sections are directly or indirectly connected to each other, and wherein said microwave surgical instrument is adapted for performing hemostasis, coagulation, fixation, and/or sealing of a polypous biological tissue.

4. The microwave surgical instrument according to claim 3, wherein the tips of said two opposed biological tissue contact sections are connected to each other via a wire.

5. The microwave surgical instrument according to claim 1, wherein the support is capable of being used as a dissector and said microwave surgical instrument is capable of dissecting a tissue.

6. The microwave surgical instrument according to claim 1, wherein said support is in the shape of a tweezer, and wherein said one or a plurality of biological tissue contact sections of element (b)(iv) comprises two biological tissue contact sections that are opposite to each other and are configured to grip a biological tissue, and wherein said microwave surgical instrument is configured for use in tweezing a tissue.

7. The microwave surgical instrument according to claim 1, wherein said support is configured as a forceps or a sealing unit, and wherein said one or a plurality of biological tissue contact sections of element (b)(iv) comprises two biological tissue contact sections that are opposite to each other to allow gripping a biological tissue, and wherein said microwave surgical instrument is configured for use in hemostasis, coagulation, fixation, cutting and/or sealing of a biological tissue.

8. The microwave surgical instrument according to claim 1, wherein said support is in the form of a scissor, and wherein said one or a plurality of biological tissue contact sections of element (b)(iv) comprises two biological tissue contact sections that are opposite to each other to allow cutting a biological tissue, and wherein said microwave surgical instrument is configured for use as scissors.

9. The microwave surgical instrument according to claim 1, wherein said support is configured to be used as a dissector, and wherein said microwave surgical instrument is adapted for dissecting a tissue.

10. A microwave surgical instrument, comprising:
(i) a microwave transmitting section comprising a coaxial cable including an internal conductor;
(ii) a coaxial body comprising:
  (a) a central conductor connected to said microwave transmitting section and to said internal conductor,
  (b) an insulator covering at least a portion of said central conductor,
  (c) an external conductor covering at least a portion of said insulator,
  (d) one or a plurality of biological tissue contact section comprising:
    (A) an exposed section of central conductor,
    (B) an insulator surface on both sides of an exposed section of central conductor, and
    (C) an external conductor end substantially parallel to said exposed section of central conductor, wherein said external conductor end being located on outside of said insulator surface; and
(iii) a support for supporting said coaxial body,
wherein a diameter of said central conductor at a tip of said coaxial body is smaller than a diameter of said central conductor at said coaxial body that is connected to said microwave transmitting section, and wherein said central conductor of said biological tissues contact section is exposed in a major axis direction, and wherein a ratio between a diameter of a tip of said central conductor at a tip of said coaxial body and a diameter of said central conductor at said coaxial body connected to said microwave transmitting section is same as a ratio between an inner diameter of said external conductor at the tip of said coaxial body and an inner diameter of said external conductor at said coaxial body connected to said microwave transmitting section.

11. The microwave surgical instrument according to claim 10, wherein said one or a plurality of biological tissue contact sections of element (ii)(d) comprises two biological tissue contact sections that are juxtaposed to each other.

12. The microwave surgical instrument according to claim 10, wherein said one or a plurality of biological tissue contact sections of element (ii)(d) comprises two biological tissue contact sections that are opposed to each other.

13. The microwave surgical instrument according to claim 10 further comprising a sealing unit for sealing a biological tissue.

14. The microwave surgical instrument according to claim 10, wherein said instrument comprises two biological tissue contact sections that are opposed to each other and having external conductor ends that are connected to each other.

15. The microwave surgical instrument according to claim 10, wherein said support comprises a surgical instrument, and wherein said coaxial body is proximate to and substantially parallel with an edge or a blade edge line of said surgical instrument.

16. The microwave surgical instrument according to claim 15, wherein said one or a plurality of biological tissue contact sections of element (ii)(d) of said coaxial body comprises two insulator surfaces forming an acute angle.

17. The microwave surgical instrument according to claim 16, wherein said two insulator surfaces forming an acute angle are attached to said surgical instrument.

18. The microwave surgical instrument according to claim 10, wherein the support is in the form of tweezers, and two biological tissue contact sections are opposite to each other to grip a biological tissue, and the microwave surgical instrument is for tweezing.

19. The microwave surgical instrument according to claim 10, wherein said support is configured as a forceps or a sealing unit, and wherein said one or a plurality of biological tissue contact sections of element (ii)(d) comprises two biological tissue contact sections that are opposed to each other to allow gripping a biological tissue, and wherein said microwave surgical instrument is configured for use in hemostasis, coagulation, fixation, cutting and/or sealing of a biological tissue.

20. The microwave surgical instrument according to claim 10, wherein said support is configured as a scissors, and said one or a plurality of biological tissue contact sections of element (ii)(d) comprises two biological tissue contact sections that are opposed to each other to allow cutting a biological tissue, and wherein said microwave surgical instrument is configured for use as a scissors.

* * * * *